(12) United States Patent  
Eder

(10) Patent No.: US 10,130,842 B2
(45) Date of Patent: Nov. 20, 2018

(54) FITNESS SYSTEMS AND METHODS THEREOF

(71) Applicant: INCLUDEFITNESS, INC., Columbus, OH (US)

(72) Inventor: James Ryan Eder, Columbus, OH (US)

(73) Assignee: INCLUDEFITNESS, INC., Columbus, OH (US)

( * ) Notice: Subject to any disclaimer, the term of this patent is extended or adjusted under 35 U.S.C. 154(b) by 488 days.

(21) Appl. No.: 14/717,011

(22) Filed: May 20, 2015

(65) Prior Publication Data

US 2015/0335951 A1 Nov. 26, 2015

Related U.S. Application Data

(60) Provisional application No. 62/001,396, filed on May 21, 2014, provisional application No. 62/153,614, filed on Apr. 28, 2015.

(51) Int. Cl.
*A63B 24/00* (2006.01)
*A63B 21/062* (2006.01)
(Continued)

(52) U.S. Cl.
CPC ........ *A63B 24/0062* (2013.01); *A63B 21/062* (2013.01); *A63B 24/0087* (2013.01); *G06F 19/3418* (2013.01); *A63B 21/0058* (2013.01); *A63B 21/00072* (2013.01); *A63B 21/015* (2013.01); *A63B 21/0628* (2015.10); *A63B 21/159* (2013.01); *A63B 21/4035* (2015.10);
(Continued)

(58) Field of Classification Search
CPC ............ A63B 24/0062; A63B 24/0087; A63B 21/062; A63B 2208/0204; A63B 2071/068; A63B 2071/065; A63B 2071/0018; A63B 21/015; A63B 21/0058; A63B 2230/75; A63B 2208/0233; A63B 2225/50; A63B 21/4043; A63B 21/159; A63B 2225/54; A63B 21/00072; A63B 2225/20; A63B 2225/15; A63B 2225/096; A63B 2220/806; A63B 2220/10; A63B 2071/0655; A63B 2024/0071; A63B 2024/0068; A63B 2022/002; A63B 21/0628; A63B 21/4035; A63B 22/0664; A63B 22/0076; A63B 22/0056; A63B 22/0023; A63B 24/0075; A63B 2220/20; A63B 22/0605; A63B 22/02; A63B 2220/17; G06F 19/3418

See application file for complete search history.

(56) References Cited

U.S. PATENT DOCUMENTS 1,922,418 A 8/1933 Conant
4,010,948 A 3/1977 Deluty
(Continued)

OTHER PUBLICATIONS

International Search Report and Written Opinion received for International Application No. PCT/US2015/031888, dated Aug. 14, 2015, 14 pages.

*Primary Examiner* — Sundhara Ganesan
(74) *Attorney, Agent, or Firm* — Ulmer & Berne LLP

(57) ABSTRACT

Systems and methods for fitness tracking are provided. An exercise apparatus is in networked communication with a fitness tracking computing system. The configuration and location of movable components of the exercise apparatus is determined based on sensors. This information is provided to the fitness tracking computing system via networked communication.

8 Claims, 15 Drawing Sheets

(51) Int. Cl.

| | | |
|---|---|---|
| *G06F 19/00* | (2018.01) | |
| *A63B 22/02* | (2006.01) | |
| *A63B 22/06* | (2006.01) | |
| *A63B 21/00* | (2006.01) | |
| *A63B 22/00* | (2006.01) | |
| *A63B 71/06* | (2006.01) | |
| *A63B 21/005* | (2006.01) | |
| *A63B 21/015* | (2006.01) | |
| *A63B 71/00* | (2006.01) | |

(52) U.S. Cl.
 CPC ....... *A63B 21/4043* (2015.10); *A63B 22/0023* (2013.01); *A63B 22/0056* (2013.01); *A63B 22/0076* (2013.01); *A63B 22/02* (2013.01); *A63B 22/0605* (2013.01); *A63B 22/0664* (2013.01); *A63B 24/0075* (2013.01); *A63B 2022/002* (2013.01); *A63B 2024/0068* (2013.01); *A63B 2024/0071* (2013.01); *A63B 2071/0018* (2013.01); *A63B 2071/065* (2013.01); *A63B 2071/068* (2013.01); *A63B 2071/0655* (2013.01); *A63B 2208/0204* (2013.01); *A63B 2208/0233* (2013.01); *A63B 2220/10* (2013.01); *A63B 2220/17* (2013.01); *A63B 2220/20* (2013.01); *A63B 2220/806* (2013.01); *A63B 2225/096* (2013.01); *A63B 2225/15* (2013.01); *A63B 2225/20* (2013.01); *A63B 2225/50* (2013.01); *A63B 2225/54* (2013.01); *A63B 2230/75* (2013.01)

(56) References Cited

U.S. PATENT DOCUMENTS

| | | |
|---|---|---|
| 4,411,424 A | 10/1983 | Barnett |
| 4,828,257 A | 5/1989 | Dyer et al. |
| 4,898,381 A | 2/1990 | Gordon |
| 5,102,122 A | 4/1992 | Piane et al. |
| 5,123,886 A | 6/1992 | Cook |
| 5,277,685 A | 1/1994 | Gonzales |
| D347,584 S | 6/1994 | Vogelpohl |
| 5,603,682 A | 2/1997 | Grider |
| 6,033,350 A | 3/2000 | Krull |
| 6,120,421 A | 9/2000 | Kuo |
| 6,224,519 B1 | 5/2001 | Doolittle |
| 6,238,323 B1 | 5/2001 | Simonson |
| 6,443,877 B1 | 9/2002 | Hoecht et al. |
| 6,443,878 B1 | 9/2002 | Webber |
| 6,599,223 B2 | 7/2003 | Wang et al. |
| 7,166,066 B2 | 1/2007 | Webber |
| 7,179,209 B2 | 2/2007 | Sechrest et al. |
| 7,282,016 B2 | 10/2007 | Simonson |
| 7,335,141 B2 | 2/2008 | Piane |
| 7,485,076 B2 | 2/2009 | Lee |
| 7,584,899 B2 | 9/2009 | de Pauw et al. |
| 7,592,923 B2 | 9/2009 | Lax |
| 7,722,509 B2 | 5/2010 | Eder |
| 8,371,164 B2 | 2/2013 | Sneek |
| D677,180 S | 3/2013 | Plitkins et al. |
| 8,448,507 B2 | 5/2013 | Salmi et al. |
| D687,047 S | 7/2013 | Hales et al. |
| 8,489,243 B2 | 7/2013 | Fadell et al. |
| D687,851 S | 8/2013 | Sloo et al. |
| D700,075 S | 2/2014 | Bould et al. |
| D708,274 S | 7/2014 | Eder |
| 2002/0025888 A1 | 2/2002 | Germanton et al. |
| 2003/0045406 A1 | 3/2003 | Stone |
| 2004/0029688 A1 | 2/2004 | Webber et al. |
| 2005/0272573 A1 | 12/2005 | Carter |
| 2006/0105893 A1 | 5/2006 | Chen |
| 2006/0205571 A1 | 9/2006 | Krull |
| 2006/0217245 A1 | 9/2006 | Golesh et al. |
| 2006/0240956 A1 | 10/2006 | Piane |
| 2007/0033068 A1 | 2/2007 | Rao et al. |
| 2007/0072748 A1 | 3/2007 | Lee |
| 2007/0161472 A1 | 7/2007 | Drechsler |
| 2007/0213185 A1 | 9/2007 | Habing |
| 2007/0219059 A1 | 9/2007 | Schwartz et al. |
| 2011/0118089 A1 | 5/2011 | Ellis |
| 2012/0130546 A1 | 5/2012 | Matas et al. |

FITNESS SYSTEMS AND METHODS THEREOF

CROSS-REFERENCE TO RELATED APPLICATIONS

This application claims the benefit of U.S. provisional patent application Ser. No. 62/001,396, filed on May 21, 2014, entitled, FITNESS SYSTEMS AND METHODS THEREOF, the disclosure of which is hereby incorporated by reference in its entirety.

BACKGROUND

Many pieces of exercise equipment, when utilized regularly, are very useful for weight loss, for improving cardiovascular stamina, and for strengthening various muscles. Some exercise equipment can be used for rehabilitative or therapeutic purposes.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
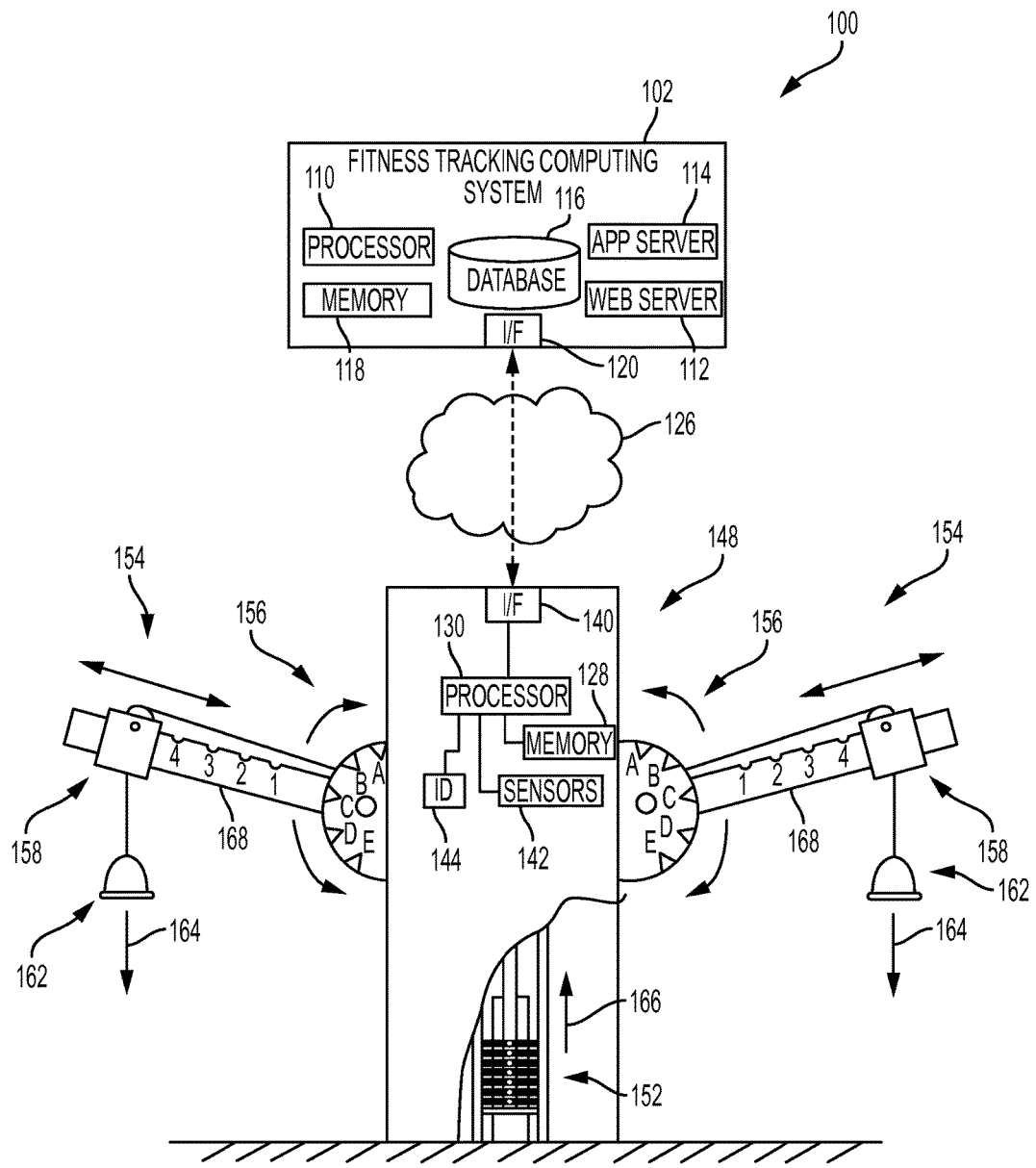
FIG. 1 depicts a simplified example block diagram of an example fitness tracking computing system in communication with an example exercise apparatus.

Various non-limiting embodiments of the present disclosure will now be described to provide an overall understanding of the principles of the structure, function, and use of systems, apparatuses, devices, and methods disclosed. One or more examples of these non-limiting embodiments are illustrated in the selected examples disclosed and described in detail with reference made to FIGS. 1-12 in the accompanying drawings. Those of ordinary skill in the art will understand that systems, apparatuses, devices, and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems, apparatuses, devices, and methods disclosed herein are described in detail by way of examples and with reference to the figures. The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and includes a wide variety of electronic information, including executable code; content such as text, video data, and audio data, among others; and various codes or flags. The terms "information," "data," and "content" are sometimes used interchangeably when permitted by context. It should be noted that although for clarity and to aid in understanding some examples discussed herein might describe specific features or functions as part of a specific component or module, or as occurring at a specific layer of a computing device (for example, a hardware layer, operating system layer, or application layer), those features or functions may be implemented as part of a different component or module or operated at a different layer of a communication protocol stack. Those of ordinary skill in the art will recognize that the systems, apparatuses, devices, and methods described herein can be applied to, or easily modified for use with, other types of equipment, can use other arrangements of computing systems, and can use other protocols, or operate at other layers in communication protocol stacks, than are described. The systems, apparatuses, devices, and methods disclosed herein generally relate to providing a platform for the planning, capturing, tracking and analyzing of activities performed by users on various types of exercise apparatuses. Additional activates facilitated by the platform can include, for example, reporting, scheduling, and maintenance tracking, which are described in more detail below. Generally, the platform comprises a coupling of rehabilitation/exercise equipment (referred to herein generally as "exercise apparatus") and associated management software and processes. Exercise apparatuses in accordance with the present disclosure can be generally configured to records every single exercise and movement completed on the equipment as exercise data. The exercise data can be collected, transmitted and stored in fitness tracking computing system. In accordance with various embodiments, a fitness tracking computing system can be HIPPA compliant and be cloud-based. Data analytics systems can be provided by a fitness tracking computing system that stores both individual and aggregate user data for monitoring, analytics, export, reporting and numerous other purposes.

Some example metrics that can be captured by systems, apparatuses, devices, and methods described herein can include time, calories, and repetitions—identifying both strong as well as weak points in user performance. The systems, apparatuses, devices, and methods described herein can also provide the ability to manually track cardiovascular routines and body weight. Interactions with the exercise equipment by users can be captured and uploaded to in fitness tracking computing system; which can then be accessible for analysis and reconfiguration to physicians, therapists, care-givers, service providers and individual users through any internet enabled device. As it to be appreciated, using the data collection techniques described herein, manual tracking and recording by a therapist or other service provider and then manually re-entered into an electronic medical records system (EMR) is reduced or eliminated.

Furthermore, as described in more detail below, users, patients, doctors, and therapists, among other types of users, can create rehabilitation and fitness routines and then track, monitor, reconfigure and oversee the outcomes and progress from these routines from anywhere via the Internet.

The systems, apparatuses, devices, and methods described herein can be used in a variety of environments and implementations. In a professional environment, for example, the platform described herein can be used for automatic recording and data export to EMR. Conventionally, a trainer or therapist manually records every set and rep performed in an exercise and then manually enters this information into a digital patient database. In accordance with the systems, apparatuses, devices, and methods described herein, this process can be streamlined and automated. In some cases, this automation can save approximately one to two hours per shift, while simultaneous enabling closer patient interaction and increased efficiencies. With the implementation of the Affordable Care Act, facilities are now required to document all activities performed and provide meaningful, measurable outcomes to such. The systems, apparatuses, devices, and methods described herein can assist with the compliance of this requirement.

Moreover, as is to be appreciated upon consideration of the present disclosure, a large amount of user data can be collected. This data can be aggregated and filtered to analyze system-wide macro trends, among other details. In some embodiments, this data can be filtered per muscle group, demographic, geography, time, industry and more to examine trends and derive information that may be useful to research facilities, insurance companies, healthcare facilities and more.

With regard to rehabilitation and fitness programming, an extensive library of exercises and workouts that can be stored by a fitness tracking computing system and assigned to patients, clients and users. These libraries can be filterable by muscle group and offer customization for therapists and other types of users. Each exercise can be offered in multiple modes: standing, sitting, and wheelchair. In some embodiments, images and videos are provided to communicate how to properly perform each exercise. Furthermore, as described in more detail below, systems, apparatuses, devices, and methods can facilitate scheduling to view patient appointments at a glance, and in some embodiments, drag and drop workouts on a calendar facilitating long term planning of routines.

As described in more detail below, the systems, apparatuses, devices, and methods can facilitate user recognition and appropriate information is pulled from a fitness tracking computing system to an exercise apparatus. After connecting to fitness tracking computing system, a list of routines can be displayed on a visual display at the exercise apparatus and a selection made by the user. In accordance with various embodiments, an exercise apparatus can guide the user step-by-step through their entire program displaying descriptive pictures, machine configuration, and resistance settings.

Various exercise data can be transmitted to the fitness tracking computing system from an exercise apparatus. This data can be arranged in clear, concise visualizations to analyze performance remotely or onsite. Professional practitioners and users can have the ability to track perform against goals, identify weak and strong areas, and adjust routines accordingly. Tools enable transparency to trends while also providing granular details down to each exercise performed can be provided to users through various dashboards and/or user interfaces.

As is to be appreciated, the systems, apparatuses, devices, and methods can beneficially permit a user to leave a healthcare environment, yet their progress and programs stay with them and are available in any other location offering exercise apparatuses in accordance with the present disclosure, such as the YMCA or local community center or health club. Alternatively, if a user is utilizing the system in a community center and then enters a healthcare environment, that information can be available to practitioners through the permission-based, HIPAA compliant allowance.

Various types of user accounts can be created and maintained by a fitness tracking computing system. In one embodiment, the account types include business accounts, professional accounts, and personal accounts. Business accounts can be for facilities and generally enable the management of multiple professionals and clients such as hospitals, rehabilitation facilities, nursing homes, etc. Numerous administrative tools can be provided to these accounts. Professional accounts can be for practitioners (for example, physicians, therapists, personal trainers and coaches) to manage multiple patient and client accounts. Personal accounts can be for individual users and can be used independently or with an associated professional.

FIG. 1 depicts a simplified example block diagram 100 of an example fitness tracking computing system 102 in communication with an example exercise apparatus 104. While only one exercise apparatus 104 is illustrated in FIG. 1, the fitness tracking computing system 102 can be in communication with any number of exercise apparatuses 104, as described in more detail below. Furthermore, the particular type and arrangement of the exercise apparatus 104 illustrated in FIG. 1 is merely for illustrative purposes, as any number of exercise apparatus types can be utilized without departing from the scope of the present disclosure.

The fitness tracking computing system 102 can be in communication with the exercise apparatus 104 over one or more networks 126, including both wireless and wireline communication networks. The fitness tracking computing system 102 can be provided using any suitable processor-based device or system, such as a personal computer, laptop, server, mainframe, mobile computer, other processor-based device, or a collection (e.g. network) of multiple computers, for example. The fitness tracking computing system 102 can include one or more processors and one or more memory units. For convenience, only one processor 110 and only one memory unit 118 are shown in FIG. 1. The processor 110 can execute software instructions stored on the memory unit 118. The processor 110 can be implemented as an integrated circuit (IC) having one or multiple cores. The memory unit 118 can include volatile and/or non-volatile memory units. Volatile memory units can include random access memory (RAM), for example. Non-volatile memory units can include read-only memory (ROM) as well as mechanical non-volatile memory systems, such as a hard disk drive, optical disk drive, or other non-volatile memory. The RAM and/or ROM memory units can be implemented as discrete memory ICs.

The memory unit 118 can store executable software and data. When the processor 110 of the fitness tracking computing system 102 executes the software instructions of various modules, the processor 110 can be caused to perform the various operations of the fitness tracking computing system 102. The various operations of the fitness tracking computing system 102 can include communicating with the exercise apparatus 104, transmitting data to the exercise apparatus 104, receiving data from the exercise apparatus 104, receiving data from a third party computing system (see e.g., computing device 910 shown in FIG. 9), transmitting data from to a third party computing system, as well as providing various types of graphical interfaces and portals for accessing and managing data stored or processed by the fitness tracking computing system 102, as described in more detail below.

The fitness tracking computing system 102 can store and access data in a variety of databases 116. The data stored in the databases 116 can be stored in a non-volatile computer memory, such as a hard disk drive, read only memory (e.g. a ROM IC), or other types of non-volatile memory. In some embodiments, one or more databases of the databases 116 can be stored on a remote electronic computer system and can be accessed by the fitness tracking computing system 102 via a network 126. At least some of the data stored in the databases 116 can be stored in compliance with relevant privacy considerations. As one having ordinary skill in the art would appreciate, a variety of other databases or other types of memory storage structures can be utilized or otherwise associated with the fitness tracking computing system 102.

Also shown in FIG. 1, the fitness tracking computing system 102 can include one or more computer servers, which can include one or more web servers, one or more application servers, and/or other types of servers. For convenience, only one web server 112 and one application server 114 are depicted in FIG. 1, although one having ordinary skill in the art would appreciate that the disclosure is not so limited. The servers 112,114 can cause content to be sent to the exercise apparatus 104, or other computing devices, via the network 126 in any of a number of formats. The servers 112, 114 can be comprised of processors (e.g. CPUs), memory units (e.g. RAM, ROM), non-volatile storage systems (e.g. hard disk drive systems), and other elements. The servers 112, 114 may utilize one or more operating systems including, but not limited to, Solaris, Linux, Windows Server, or other server operating systems.

In some embodiments, the web server 112 can provide a graphical web user interface through which various users can interact with the fitness tracking computing system 102, examples of which are described in more detail below with regard to FIGS. 9 and 10A-E. The graphical web user interface can also be referred to as a graphical user interface, client portal, client interface, graphical client interface, and so forth. The web server 112 can accept requests, such as HTTP requests, from clients and serve the clients responses, such as HTTP responses, along with optional data content, such as web pages (e.g. HTML documents) and linked objects (such as images, video, documents, data, and so forth). The application server 114 can provide a user interface for users who do not communicate with the fitness tracking computing system 102 using a web browser. Such users can have special software installed on their computing device to allow the user to communicate with the application server 114 via the network 126.

The fitness tracking computing system 102 can be in communication with the exercise apparatus 104, respectively, via the network 126, using a suitable communications interface 120. The network 126 can be an electronic communications network and can include, but is not limited to, the Internet, LANs, WANs, GPRS networks, other networks, or combinations thereof. The network 126 can include wired, wireless, fiber optic, other connections, or combinations thereof. In general, the network 126 can be any combination of connections and protocols that will support communications between the fitness tracking computing system 102 and the exercise apparatus 104. Data communicated via the network 126 can be of various formats and can include, for example, textual, visual, audio, written language, other formats or combinations thereof. The nature of data and messages communicated via the network 126 will be discussed in further detail in association with other exemplary embodiments.

Still referring to FIG. 1, the exercise apparatus 104 can have associated memory, schematically illustrated as memory 128 and one or more processors, schematically shown as processor 130. The exercise apparatus 104 can also include one or more communications interfaces 140 for communicating with fitness tracking computing system 102.

The exercise apparatus 104 can also have one or more sensors 142 and a user identification system 144, as described in more detail below. The exercise apparatus 104 can also have a housing 148 that contains a resistance assembly 152. The present disclosure is not intended to be limited to any particular type or arrangement of resistance assembly 152. The resistance assembly 152 can be provided through any suitable technique, such as a moveable weight stack, one or more resistance bands, one or more resistance rods, one or more resistance motors, a friction-based resistance assembly (i.e., as may be used with a stationary bike), a solenoid tower, and so forth. Additional details regarding an example solenoid tower can be found in U.S. Pat. No. 7,722,509, which is incorporated herein by reference in its entirely.

The exercise apparatus 104 can also comprises one or more extension arm assemblies 154. While FIG. 1 depicts the exercise apparatus 104 having two extension arm assemblies 154, this disclosure is not so limited. Depending on the type of exercises facilitated by the exercise apparatus 104, any number of extension arm assemblies 154 having any suitable configuration can be utilized. In some embodiments, the extension arm assembly 154 can be movable relative to the housing 148, as indicated by arrows 156. Furthermore, while arrows 156 depict rotational movement, other embodiments can have one or more extension arm assemblies that slide, hinge, articulate, or otherwise translate relative to the housing 148. As described in more detail below, the particular location of the extension arm assembly 154 can be based on the particular exercise that is being performed by a user of the exercise apparatus 104. In some embodiments, the extension arm assembly 154 can also comprise a shuttle 158 that is configured to translate along a track 168 of the extension arm assembly 154. One or more grips 162 can be linked to the resistance assembly 152. In the illustrated embodiment, when the grips 162 are moved in the direction indicated by arrow 164, weights of the resistance assembly 152 are pulled in the directed indicated by arrow 166. However, while FIG. 1 illustrates the grips 162 as a hand grip, in other embodiments the grip can be one or more bars, handlebars, pedals, or any other suitable device.

Utilizing the sensors 142, various data regarding the extension arm assemblies 154 can be obtained by the exercise apparatus 104, and in some instances, provided to the fitness tracking computing system 102. Example types of data can include extension arm assembly 154 position, movement of the extension arm assembly 154, repetition data, set data (i.e., groupings of repetitions of a particular exercise movement), resistance amount, timing data, travel distance, data regarding the movement and/or position of the shuttle 158, movement of the grips 164, and so forth. The data can be segmented based on the particular components of the exercise apparatus that the user is moving.

In some embodiments, a visual display can be used to convey various information to a user. The visual display can be, for example, local to the exercise apparatus 104, such as mounted on the housing 48. Additionally or alternatively, the visual display can be provided by another device viewable by a user, such as a smart phone, tablet computer, or a laptop, for example, that is in communication with the exercise apparatus 104 and/or the fitness tracking computing system 102. The displayed information can be, for example, a welcome screen, user information, exercise instructional data (text, graphics, audio, and/or video), an exercise status summary, a set count, a repetition count, an indication of resistance, as well as any other status or informational content (e.g., caloric data), as may be desirable. While a visual display is described herein, it is to be appreciated that some embodiments can alternatively or additionally include audio-based devices for conveying information to a user.

In accordance with some embodiments, a user can interact with the user identification system 144 upon approaching the exercise apparatus 104. The user identification system 144 can facilitate identification of the user based on user-provided information. Examples of user-provided information comprises, without limitation, data provided from a key or dongle (such as an RFID tag), biometric data, a coded input, and so forth. Upon receiving the identification data, the user identification data can be provided to the fitness tracking computing system 102 over the network 126 by the exercise apparatus 104. In some embodiments, a user's name is not provided through the network in order to mitigate privacy concerns. In addition to the user identification data, machine data from the exercise apparatus 104 can also be provided to the fitness tracking computing system 102. Upon receiving the user identification data, the fitness tracking computing system 102 can access one or more record stored in a database 116. The record in the database 116 can indicate one or more exercise protocols for the user, as well has other fitness related data. The exercise protocol can comprise, for example, one or more exercises to be performed on the exercise apparatus 104 at a particular resistance level. The exercise protocol can then be transmitted by the fitness tracking computing system 102 and received by the exercise apparatus 104. In some embodiments, the fitness tracking computing system 102 can determine the last exercise performed by that user (either at that machine or a different machine) and ask the user if they wish to continue that workout regimen.

In any event, instructional content can be displayed on a visual display indicating, for example, an instruction for a first exercise. In one embodiment, the instruction content comprises positional information for the extension arm assembly 154 that is correlated to a particular exercise type. In this fashion, the exercise apparatus 104 can be used to facilitate a plurality of different types of exercise through different positions of the extension arm assemblies 154. The user can then manipulate the extension arm assembly 154 as instructed. Depending on the configuration of the exercise apparatus 104, such manipulation can include rotating the track 168 to a particular angle and/or setting and then sliding the shuttle 158 to a particular detent or position along the track 168. Using the sensors 142, the exercise apparatus 104 can monitor the configuration of the extension arm assembly 154 to determine if the user has the extension arm assembly 154 in the proper position to perform the instructed exercise. If the user has not properly configured the exercise apparatus 104 for the instruction exercise, appropriate notices (graphical and/or auditory) can be provided to the user. In some embodiments the sensors 142 can include one or more optical sensors (i.e., cameras) that can be used to monitor a user's movement, position, stance, etc. during a particular instructed exercise. Depending on the configuration of the resistance assembly 152, the instructed resistance can be automatically selected by the exercise apparatus 104 (i.e., using a solenoid tower), or the user can select the instructed resistance.

In one embodiment, once it is determined from the signals received form the sensors 142 that the exercise apparatus 104 is properly configured, the visual display will indicate that exercise can be commenced. When a user performs the exercise, one or more exercise event signals are generated by one or more sensors 142. These exercise event signals can be received and processed by the processor 130. Using these signals, exercise data can be tracked and logged locally at the exercise apparatus 104 and/or at the fitness tracking computing system 102. Furthermore, if the exercise apparatus 104 comprises a plurality of extension arms assemblies 154, the use of each extension arm assemblies 154 can be individually monitored and tracked. Accordingly, for exercise apparatuses 104 have a first extension arm assembly 154 for a left arm and a second extension arm assembly 154 for a right arm (as shown in FIG. 1), the movements of the exercises using the left and right arm can each be individually tracked and monitored.

As a user is performing the exercise, the visual display can provide an exercise status summary that comprises, for example, set data, repetition data, repetition data, timing data, and/or other type of fitness-related data (such as caloric data and/or left arm vs. right arm data), and so forth. This data can be based on, for example, the signals received from the sensors 142 and provided to the processor 130. Similar data can also be provided to the fitness tracking computing system 102 so the exercise profile associated with that user can be updated, as described in more detail below. In some embodiments, when the user eventually walks away from the exercise apparatus 104, stops interacting with the apparatus, or expressly "logs out," the data collection for that exercise session will cease.

Figure 2A:
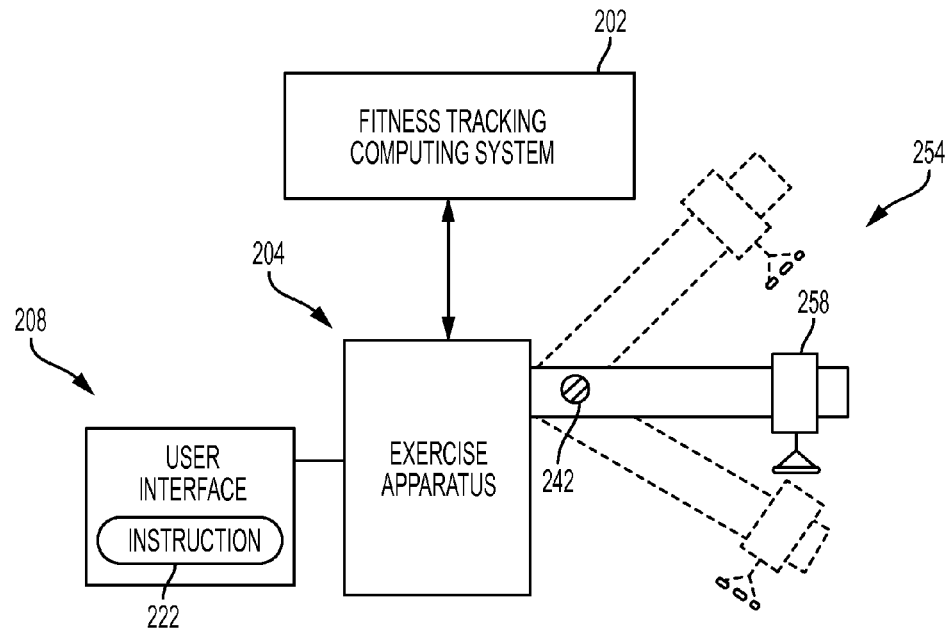
FIGS. 2A-2B depict an example exercise apparatus having a positionable extension arm assembly.
Figure 2B:
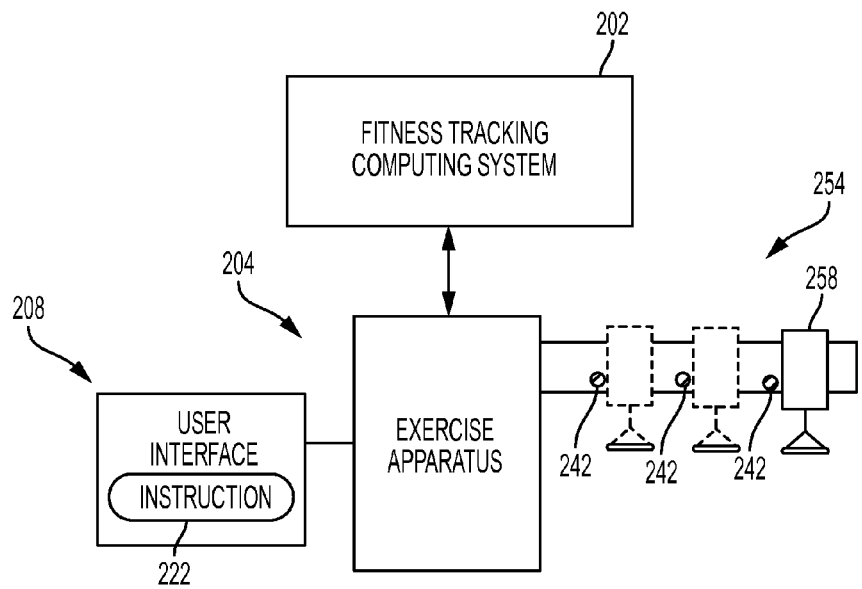

FIGS. 2A-2B depict an example exercise apparatus 204 having a positionable extension arm assembly 254. Similar to the exercise apparatus 104 of FIG. 1, the exercise apparatus 204 is in communication with a fitness tracking computing system 202. A user interface 208 can be used to provide an instruction 222 that is received from the fitness tracking computing system 202. The content of the instruction 222 can be based on, for example, the user of the exercise apparatus 204. The instruction 208 can indicate a first position of the extension arm assembly 254 (shown as an angular position). Upon receiving the instruction 222, the user can accordingly manipulate the extension arm assembly 254 as instructed and a signal generated by the sensor 242 can be used to determine if the extension arm assembly 254 is property positioned. The sensor 242 can be any type of suitable sensor or collection of sensors, such a proximity sensor, a rotary encoder, and so forth. Referring to FIG. 2B, the instruction 222 can also indicate a position for the shuttle 258. Similar to FIG. 2A, signals from the sensors 242 can be used to determine if the shuttle 258 has been moved to the proper position based on the instruction 222 that was provided to the user.

Furthermore, the instruction 222 can be conveyed to the user using any suitable mode, such as a visual instruction, an audio instruction, an animated instruction, a tactile instruction (i.e., braille), a text-based instruction, and/or a graphical instruction, for example. In some embodiments, the instruction 222 can provide the user with substantially real-time feedback regarding use of the exercise apparatus 204. Such feedback can include, without limitation, an indication for a user to speed up, slow down, switch grips, switch stance, or pause, for example. If the exercise apparatus 204 includes optical sensing capabilities (i.e., one or more cameras), a user's movement, position, stance, etc. can be monitored and the instruction 222 can provide feedback, such as to make adjustments to posture, change speed, and so forth.

Figure 3A:
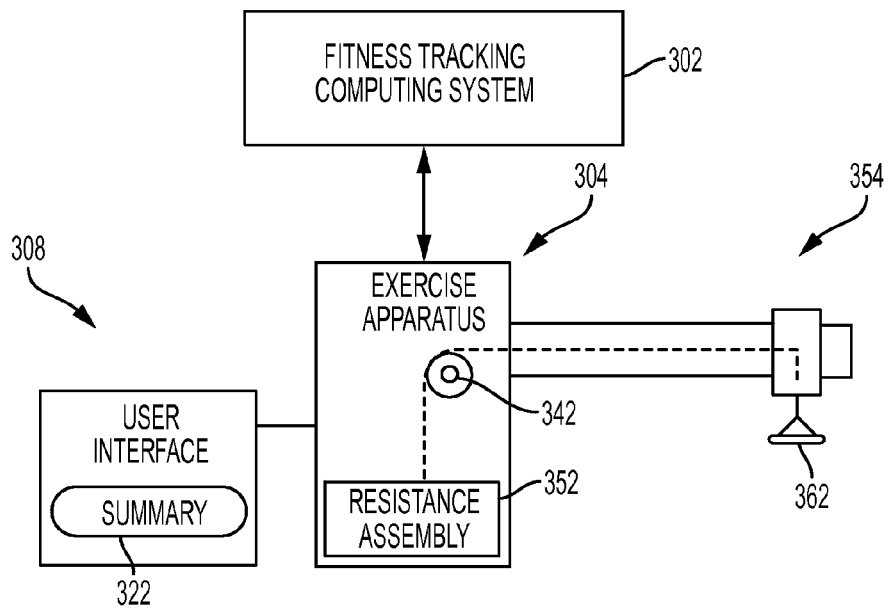
FIGS. 3A-3B depict an example exercise apparatus having a resistance assembly that is operably coupled to a grip on an extension arm assembly.
Figure 3B:
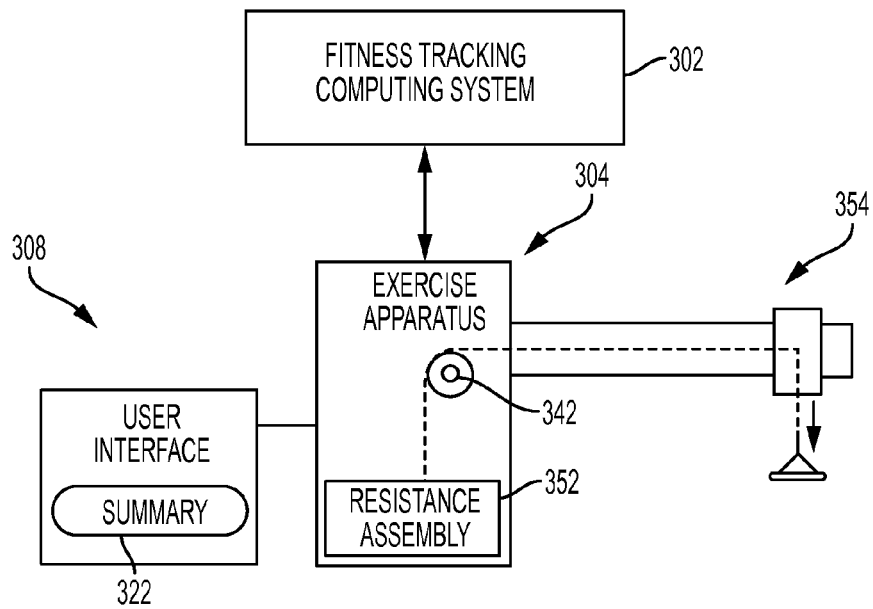

FIGS. 3A-3B depict an example exercise apparatus 304 having a resistance assembly 352 that is operably coupled to a grip 362 on an extension arm assembly 254. Similar to the exercise apparatus 104 of FIG. 1, the exercise apparatus 304 is in communication with a fitness tracking computing system 302. A user interface 308 can be used to provide an exercise summary 322 based on movement of the resistance assembly 352 and/or the grip 362. The grip 362 can be moved from the position shown in FIG. 3A to the position shown in FIG. 3B by a user pulling the grip 362 in the direction indicated by arrow 364. The summary 322 can display any variety of exercise related content, such as the resistance assembly setting, the number of repetitions, the number of sets, timing data, and so forth.

Figure 4:
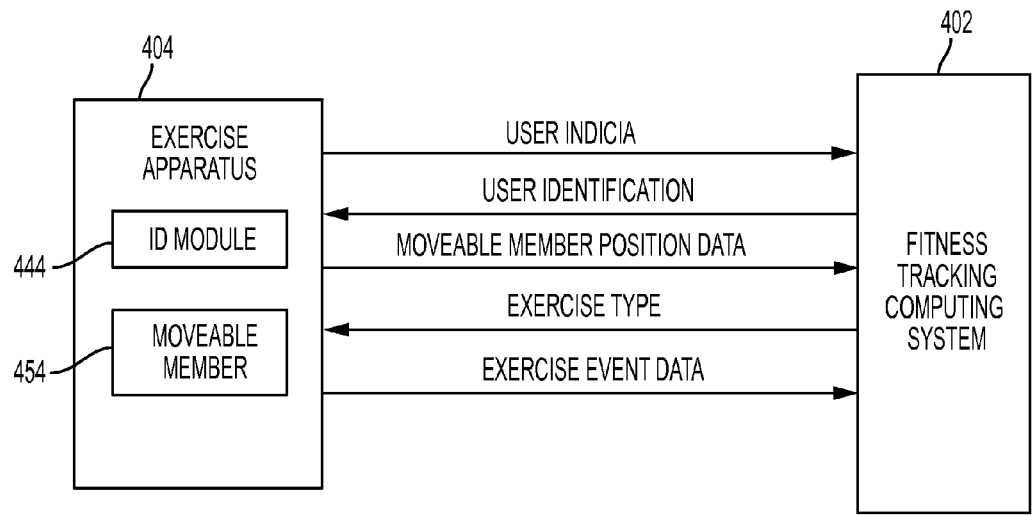
FIGS. 4-5A depict example message sequence charts showing example messaging between an exercise apparatus and a fitness tracking computing system.
Figure 5:
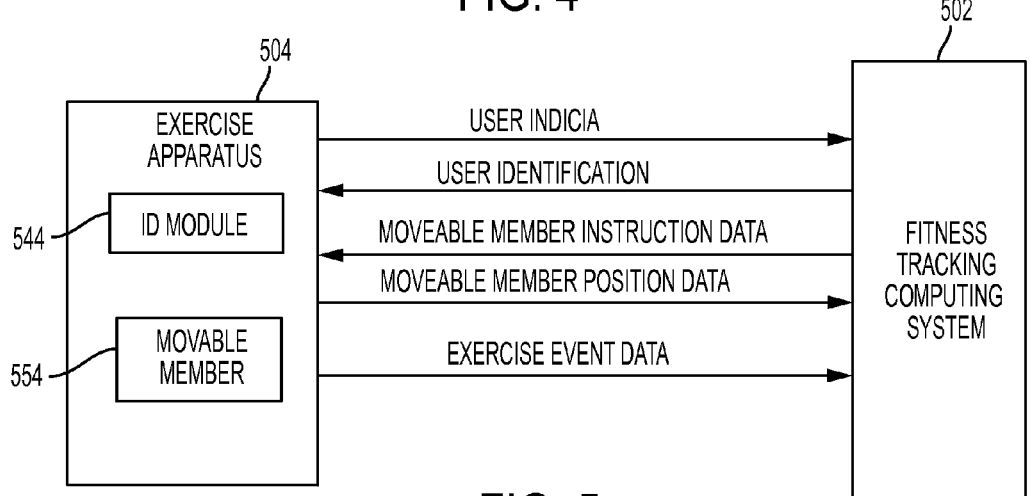

FIGS. 4-5 depict example message sequence charts between an exercise apparatus and a fitness tracking computing system. Referring first to FIG. 4, the exercise apparatus 404 has an identification module 444 that is used to receive identifying data from the user, referred to as user indicia. The identification module 444 can include, for example, a non-contacting sensor and a wireless communication identification module. For example, when a user approaches the exercise apparatus 404 the non-contact sensor can generate a signal instructing the wireless communication identification module to transmit a polling signal. In some embodiments the wireless communication identification module comprises any of a radio frequency identifier (RFID) module, an 802.11 wireless module, a Bluetooth module, or combinations thereof. Once user identifying information has been received by the exercise apparatus 104, a user indicia message can be provided to the fitness tracking computing system 402, as illustrated in FIG. 4. Once the user has been identified by the fitness tracking computing system 402, a user identification message can be sent to the exercise apparatus 404. In some embodiments, a welcome message identifying the user can be displayed to the user of the exercise apparatus 404. In FIG. 4, the user configures the exercise apparatus 404 in a user-defined configuration. Based on signals generated by one or more onboard sensors, a moveable member position data message is provided to the fitness tracking computing system 402. The moveable member position data message can, for example, identify a rotational position of the moveable member 454, a selected resistance, and so forth. Based on the moveable member position data, the fitness tracking computing system 402 can determine the type of exercise facilitated by that particular setting. An exercise type message can then be provided to the exercise apparatus 404 and information can be displayed on a user interface identifying the selected exercise type. Subsequent to a user exercising, or in substantially real-time, one or more messages comprising exercise event data can be transmitted from the exercise apparatus 404 to the fitness tracking computing system 402. This data can be used for long-term exercise tracking, insurance reporting, and other types of data aggregation, as described in more detail below.

Referring now to FIG. 5, the exercise apparatus 504 has an identification module 544 that is used to receive identifying data from the user, referred to as user indicia, similar to FIG. 4. In FIG. 5, once the user has been identified, the fitness tracking computing system 502 transmits a message comprising moveable member instruction data. This moveable member instruction data can be displayed on a user interface so the user can properly configure the exercise apparatus 504. The moveable member position data for a moveable member 554 and/or other settings can then be provided to the fitness tracking computing system 502 to confirm the user is exercising according to the instructions. Additionally, as illustrated, one or more messages comprising exercise event data can be transmitted from the exercise apparatus 504 to the fitness tracking computing system 502.

Figure 5A:
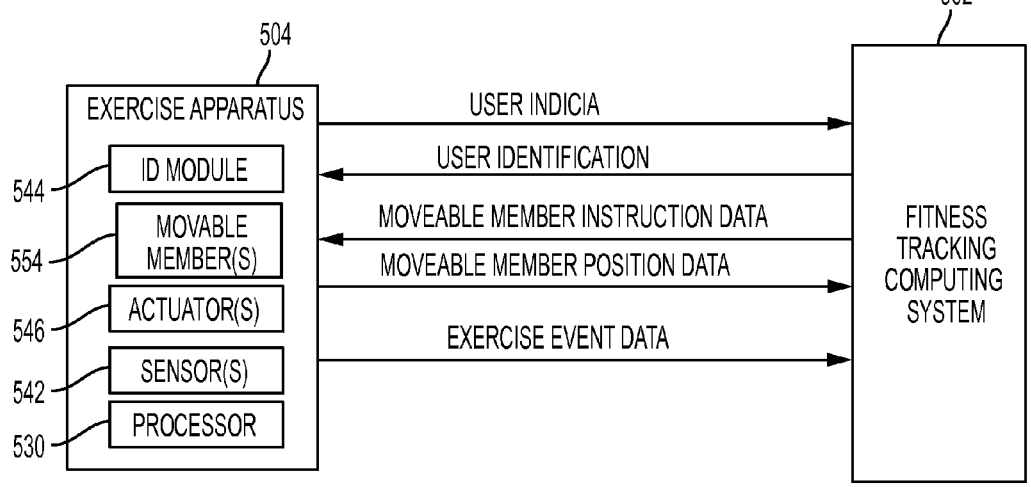

Referring now to FIG. 5 and FIG. 5A, in some embodiments, the exercise apparatus 504 is self-configuring, such that upon receipt of the moveable member instruction data, one or more components of the exercise apparatus 504 are adjusted automatically. As shown in FIG. 5A, various actuators 546, such as motors, solenoids, pistons, pumps, and the like, can be mechanically coupled to rotatable, translatable, or otherwise adjustable components of the exercise apparatus 504. The actuators 546 can be in electrical communication with a processor 530, such that when a command is received from the processor 530, one or more actuators 546 are activated to cause the movement of one or more adjustable components of the exercise apparatus 504. The particular components that are physically adjusted can depend on the particular configuration, type and/or arrangement of the exercise apparatus 504 and the particular exercise to be performed. In some embodiments, metrics of the user (such as height, reach, etc.) can be used to further determine appropriate positions of various adjustable components of the exercise apparatus 504. In some embodiments, preferences of the user (such as a preference for exercising from a seated position rather than a standing position) can be used to further determine appropriate positions of various adjustable components of the exercise apparatus 504.

While the particular components that can be self-adjusting will vary based on the type of exercise equipment, example components or features of an exercise apparatus 504 that may be adjusted, can include, but are not limited to, a seat (extend/retract and/or raise/lower), a resistance assembly (increase/decrease resistance), an extension arm assembly, a shuttle, an incline angle (i.e., for a treadmill), a back rest (extend/retract and/or raise/lower), a lap bar (extend/retract and/or raise/lower), and belt speed (i.e., for a treadmill).

In some embodiments, the processor 530 utilizes the actuators 546 to initiate movement of a particular component and then in substantially real-time determines the position based on the feedback data received from sensors 542. Once the desired feedback data is received from one or more sensors 542 to indicate the proper adjustment has been made, the actuators 546 can be deactivated. In some embodiments, the processor 530 determines the appropriate use of the actuators 546 to move a particular component based on the current position and the desired position.

While the exercise apparatus 504 can receive the adjustment commands from the fitness tracking computing system 502, in some embodiments, local inputs received from a user can be used to initiate self-configuring. For example, a user may select a particular exercise or workout routine (i.e., set of exercises) from an interface associated with the exercise apparatus 504. Based on the selection, the exercise apparatus 504 can automatically self-adjust to position the various components for the selected exercise. Upon detection of completion of a particular exercise (i.e., a successful completion of a set of repetitions), the exercise apparatus 504 can automatically self-adjust to position the various components for the next exercise type for the user.

Figure 6:
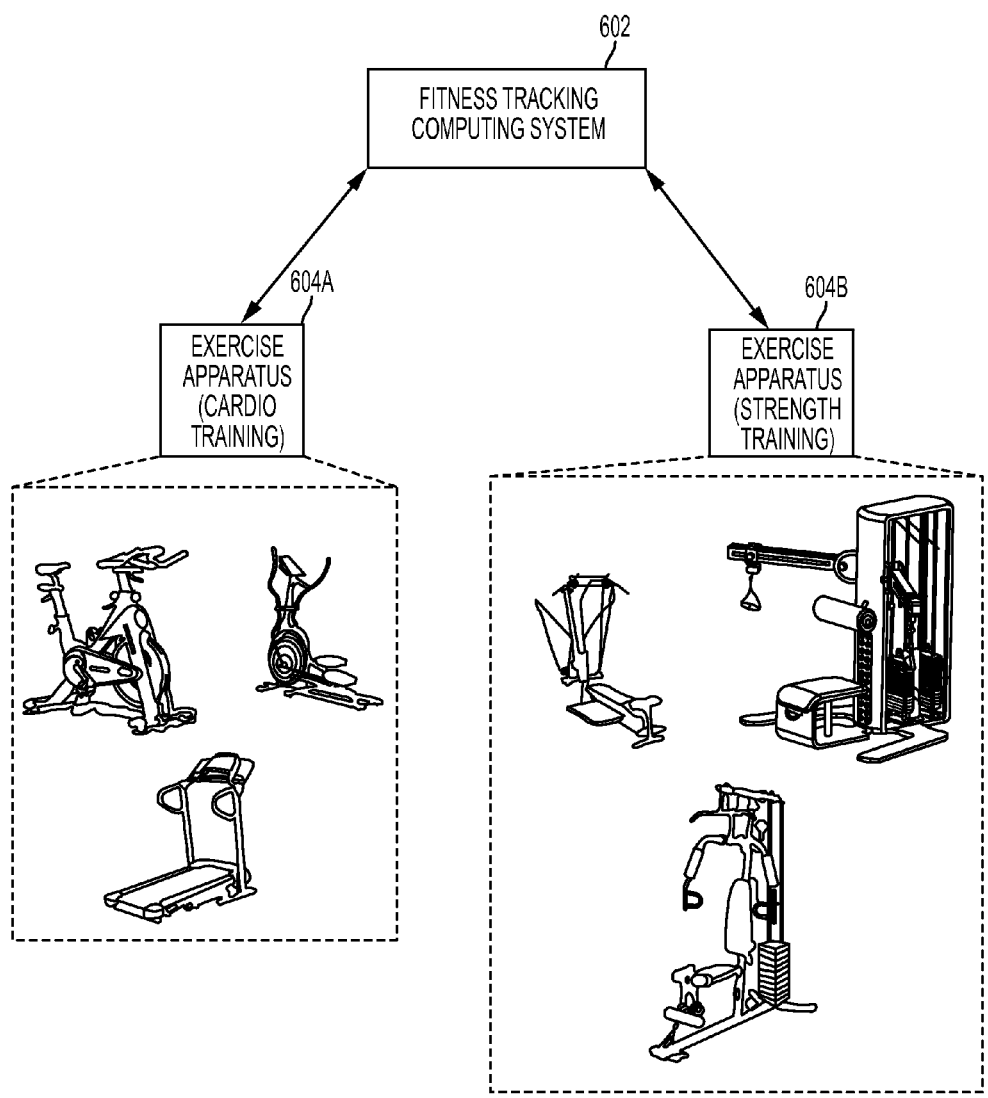
FIG. 6 schematically depicts two example subsets of exercise apparatuses that can be in communication with a fitness tracking computing system.

The systems, methods, and apparatuses described herein can be used in combination with a wide variety of exercise apparatuses. FIG. 6 schematically depicts two example subsets of exercise apparatuses that can be in communication with a fitness tracking computing system 602. For the purposes of illustration, the exercise apparatuses are separated into cardio training exercise apparatuses 604A and strength training exercise apparatuses 604B. Cardio training exercise apparatuses 604A can include, without limitation, stationary bikes, treadmills, elliptical machines, stair climbers, rowing machines and the like. Strength training exercise apparatuses 604B can include, without limitation, multi-station machines, circuit machines, home-gym machines, universal machines, and the like. In any event, the cardio training exercise apparatuses 604A and strength training exercise apparatuses 604B can be configured to identify users and communicate with the fitness tracking computing system 602 for fitness tracking purposes, as described herein.

Figure 7:
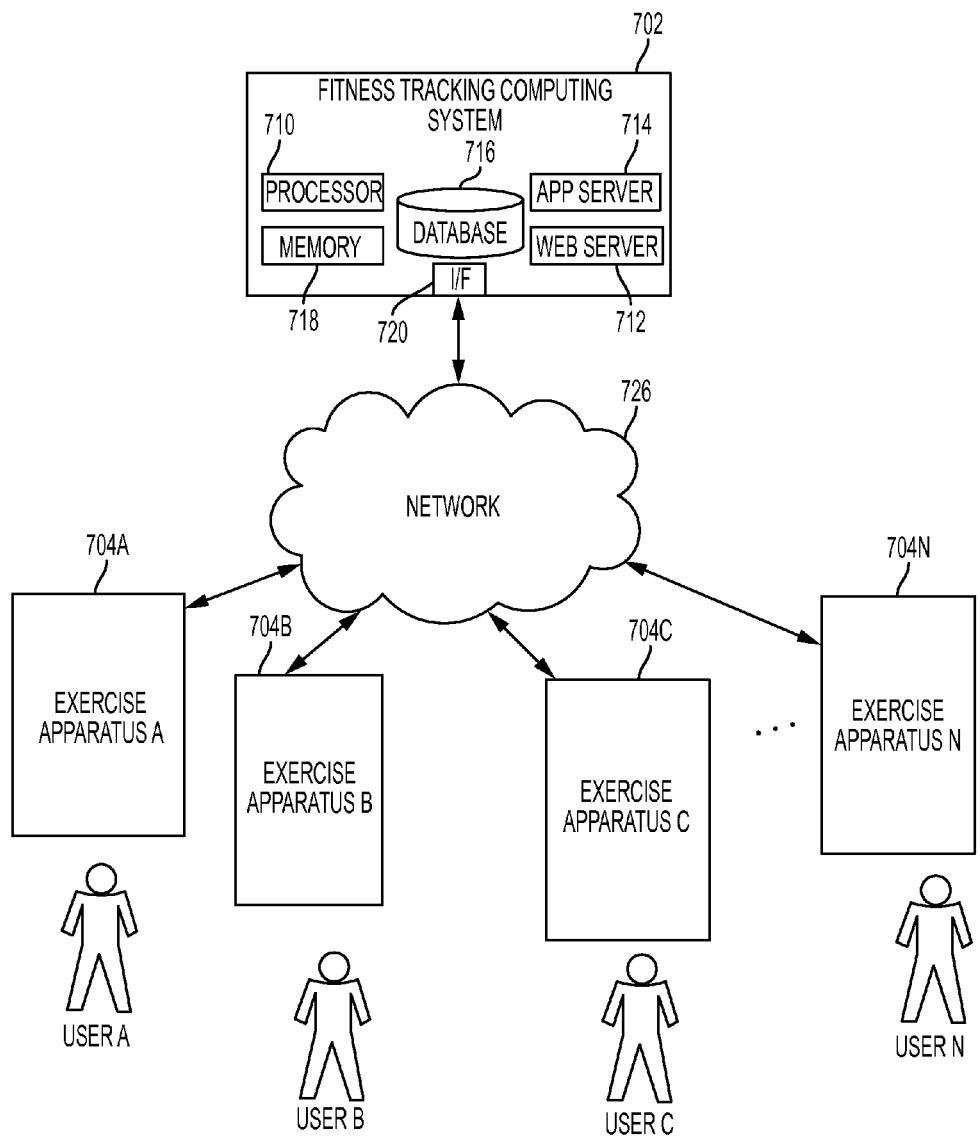
FIG. 7 depicts an example system diagram of a fitness tracking computing system in communication with a plurality of exercise apparatuses.

FIG. 7 depicts an example system diagram of a fitness tracking computing system 702 in communication with a plurality of exercise apparatuses 704A . . . 704N. The fitness tracking computing system 702 can be similar to the fitness tracking computing system 102 of FIG. 1 having a processor 710, a memory 718, a database 716, an app server 714, a web server 712, and an interface 720. As is to be appreciated, however, the fitness tracking computing system 702 can have a variety of software and hardware configurations. The fitness tracking computing system 702 is shown in network communications with each exercise apparatus 704-704N over a network 726. As shown, users can interact with each exercise apparatus (shown as users A-N). The respective exercise apparatuses can communicate identifying indicia to the fitness tracking computing system 702 from the user and the fitness tracking computing system 702, in turn, can provide exercise instructions, and other data and/or content, to the exercise apparatus.

The fitness tracking computing system 702 can also track and store the exercise data received from each use of the exercise apparatus 704-704N. Such data can be aggregated, sorted, reported, or otherwise may be processed. In some embodiments, exercise data is tied to a particular type of exercise or therapy for tracking purposes. By way of example, a certain subset of users may be interacting with one or more exercise apparatus 704-704N as part of a rehabilitative therapy regimen. Over time, the fitness tracking computing system 702 can track the user's performance and such tracking can be used to ascertain the relative effectiveness of that particular rehabilitative therapy regimen. On a broader scale, the fitness tracking computing system 702 can track the performance of a relatively large number of users (such as hundreds of users, thousands of users, or hundreds of thousands of users) and process the data based on any number of useful metrics. Such metrics or parameters may include, for example, user data, device data, demographic data, time data, exercise data, location data, market data, insurance data, and medical data. In some embodiments, a data aggregation module hosted by the fitness tracking computing system 702, or elsewhere in the system, can be used to coordinate the data processing, analytics and reporting that can be performed based on the wide variety of data collected by the exercise apparatus 704-704N. The data gathering and "big data" aggregation that is enabled by the presently disclosed system can be used in a wide variety of implementations and applications. For example, insurance companies may use the information for tracking a patient's adherence to a particular treatment regimen. A rehabilitation center may use the information to track patient performance or effectiveness of particular treatment protocols. Beneficially, a particular user's exercise data can be gathered by the fitness tracking computing system 702 across a plurality of exercise apparatus, which may be in the same physical location of different physical locations. By way of example, a particular patient may exercise on exercise apparatus 704A that is located at a medical center. That particular patient may then subsequently perform exercises on exercise apparatus 704B that is physically located at a YMCA or other facility. Both exercise apparatus 704A and exercise apparatus 704A can provide data to the fitness tracking computing system 702, and the fitness tracking computing system 702 can instruct the user to perform particular exercises irrespective of what the exercise apparatus the patient is using.

In some embodiments, the fitness tracking computing system 702 can comprise a maintenance module for facilitating on-demand and/or predictive maintenance support for the exercise apparatus 704-704N. For example, one of the exercise apparatus 704-704N can transmit an error message or other type of flag to the fitness tracking computing system 702 indicating an issue or fault. Additionally or alternatively, the use of the exercise apparatus 704-704N can be tracked (locally and/or at the fitness tracking computing system) for predictive maintenance purposes. A schedule of routine maintenance tasks can be stored and when a particular exercise apparatus 704-704N satisfies a condition, the fitness tracking computing system 702 can provide a maintenance notification. The maintenance notification can be any suitable form of notification, such as a message delivered to a portal or an electronic message can be dispatched (i.e., text message, email message, etc.), for example. The condition can be, for example, a number of repetitions performed on the exercise apparatus, an amount of time since the last maintenance task, and so forth.

Figure 8:
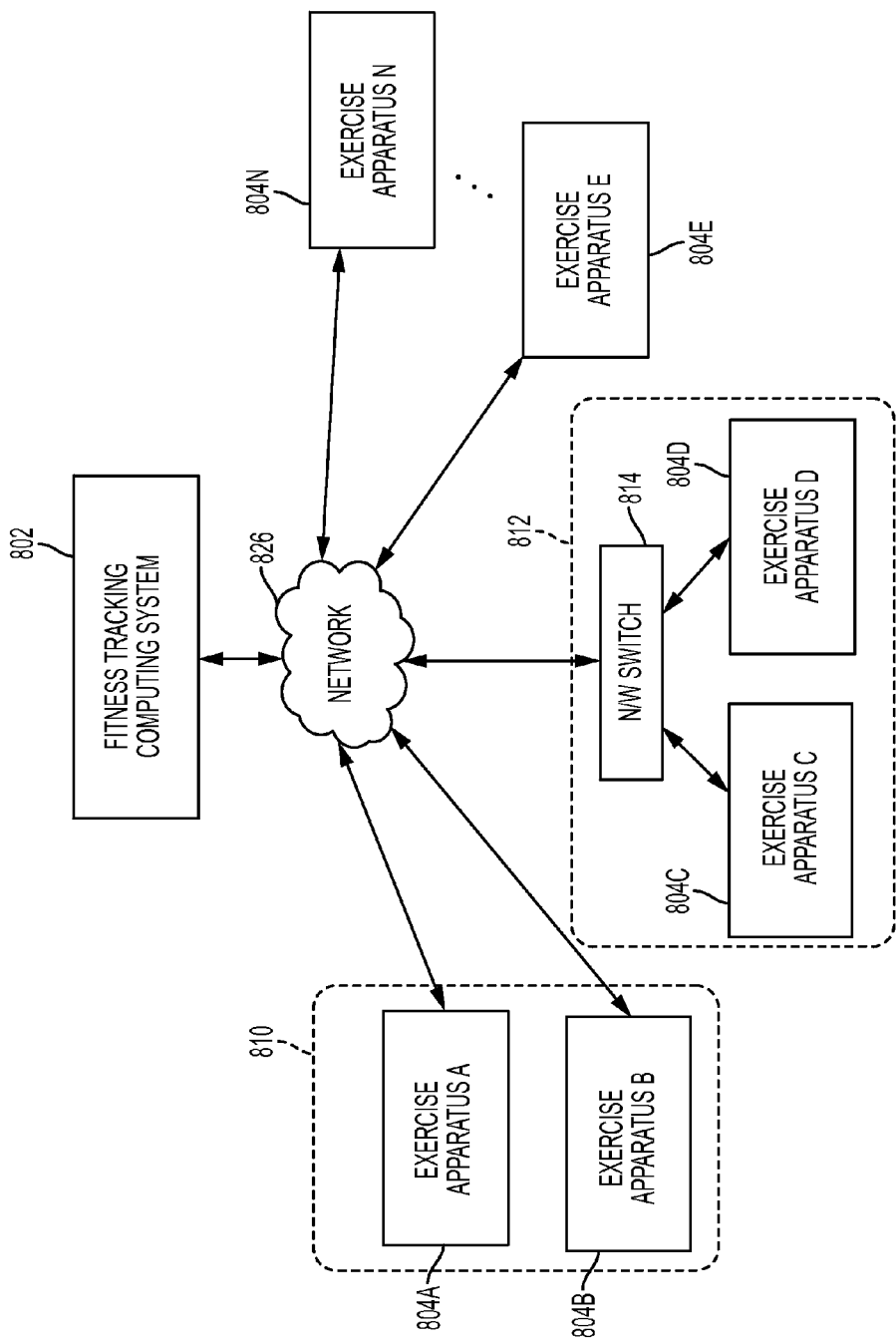
FIG. 8 depicts another example system diagram of a fitness tracking computing system in communication with a plurality of exercise apparatuses.

FIG. 8 depicts another example system diagram of a fitness tracking computing system 802 in communication with a plurality of exercise apparatuses 804A . . . 804N. The fitness tracking computing system 802 can be similar to the fitness tracking computing system 102 of FIG. 1 having a processor 810, a memory 818, a data store 870, an app server 814, a web server 812, and an interface 820. FIG. 8 schematically illustrates that in accordance with the present disclosure, the exercise apparatuses 804A . . . 804N can be positioned in a wide variety of locations or environments. Physical environment 810, for example, can be a gym or fitness center that includes exercise apparatus 804A and exercise apparatus 804B. Physical environment 812, for example, can be a medical center, hospital, or rehabilitation center that includes exercise apparatuses 804C and exercise apparatuses 804D. In the illustrated embodiment, a network switch 812 is included in the physical environment 812 to help facilitate communications between the exercise apparatus 804C and exercise apparatus 804D and the fitness tracking computing system 802. In accordance with the present disclosure, irrespective of where exercise apparatuses 804A . . . 804N is physically located, any user's interactions with the exercise apparatuses 804A . . . 804N can be monitored.

Figure 9:
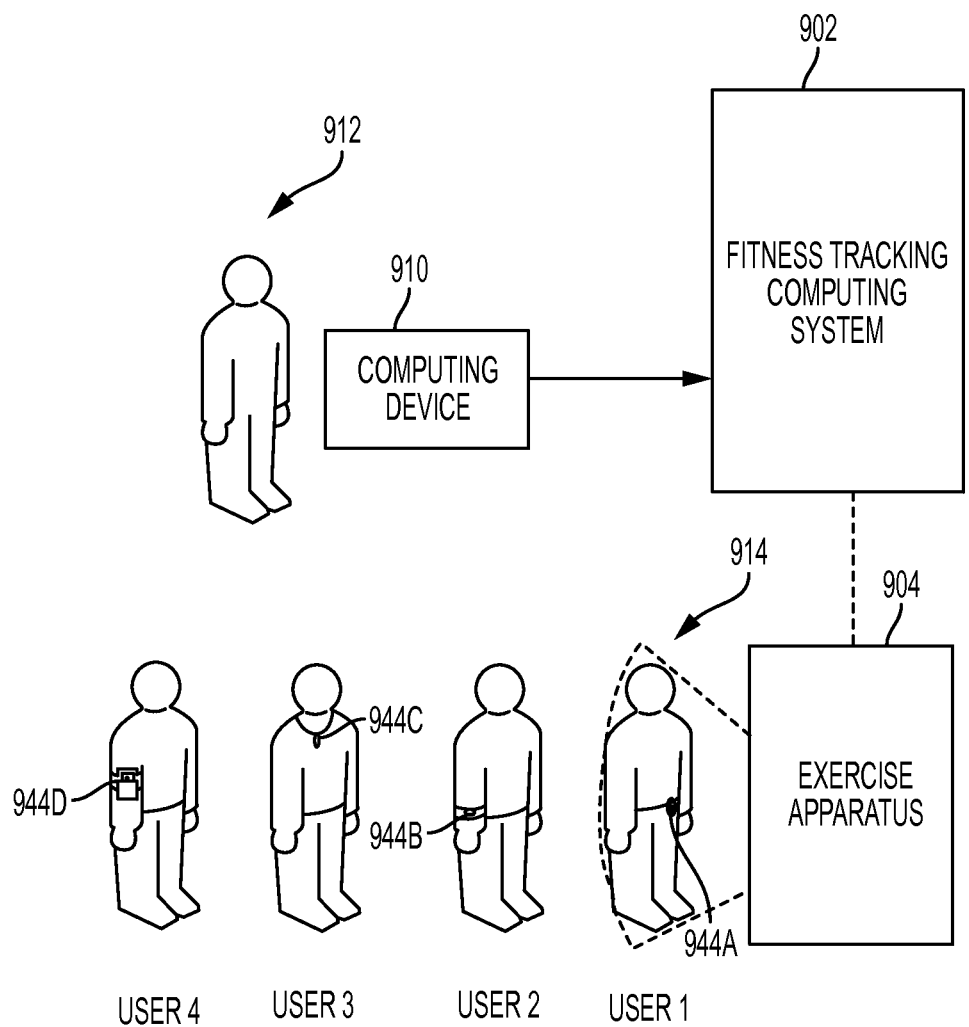
FIG. 9 depicts a system diagram of a fitness tracking computing system that is in network communication with an exercise apparatus.

FIG. 9 depicts a system diagram of a fitness tracking computing system 902 that is in network communication with an exercise apparatus 904. In the illustrated embodiment, an administrator 912 can communicate with the fitness tracking computing system 902 by way of a computing device 910. The computing device 910 can be, for example and without limitation, a desktop computer, mobile computing device, smart phone, laptop, tablet computer, and so forth. The administrator 912 can be any suitable type of user, such as a professional user, a medical professional, an exercise professional, an insurance company representative, a user of the exercise apparatus, and so forth.

In one embodiment, the administrator 912 can input or select a particular fitness or therapeutic regimen for a particular user. When that user is identified by any exercise apparatus that is in communication with the fitness tracking computing system 902, the fitness or therapeutic regimen can be transmitted to that exercise apparatus in the form of instructions to the user. The administrator 912 can also receive reports or other types of data to review a user's interactions with the exercise apparatus. In another embodiment, the administrator 912 can interact with the fitness tracking computing system 902 to schedule appointments for one or more exercise apparatuses for one or more users, as described in more detail below.

Still referring to FIG. 9, a plurality of users are depicted, shown as users 1-4. Each user has an identifying key 944. In some embodiments the identifying key may be a number or other code that the user types or otherwise provides to the exercise apparatus 904. A variety of example of identifying keys are shown in FIG. 9 Identifying key 944A is shown as a clip. Identifying key 944B is shown as a band. Identifying key 944C is shown as a necklace. Identifying keys 944A, B, C can each comprise an RFID tag, for example. Identifying key 944D is shown as a smartphone. The exercise apparatus 904 can tether to or otherwise poll the smartphone to collect user identifying information. A wide variety of other identifying keys can be used without departing from the scope of the present disclosure.

When the user is proximate to the exercise apparatus 904, the identifying key can be provided to the exercise apparatus 904. In the illustrated embodiment, the exercise apparatus 904 comprises a first sensor (such as a motion detecting circuit) that determines when a user is in an identification zone 914. When a user is in the identification zone 914, the exercise apparatus 904 can then initiate a routine that attempts to poll the identifying key 944. If a response is received from an identifying key 944, the response is provided to the fitness tracking computing system 902. The fitness tracking computing system 902 can then cross-reference the identifying key to a user database and determine one or more exercise instructions to provide to the user. During the exercise session with the exercise apparatus 904, data regarding the user's interaction can be monitored and stored. When the user leaves the identification zone 914, the user can be automatically logged out of the exercise apparatus 904 and the exercise apparatus 904 can provide the exercise data to the fitness tracking computing system 902 for long term storage and subsequent reporting.

In accordance with the present disclosure, a variety of graphical user interfaces can be presented to variety of users on a variety of different types of computing devices. FIGS. 10A-10E depict example simplified graphical user interfaces 1030, 1040, 1050, 1060, 1070 that can be presented on a display of a computing device 1010, and in some cases on a visual display of an exercise apparatus. The graphical user interfaces can be generated by a fitness tracking computing system 1002 (i.e., a web server and/or an app server) and can be provided to a user 1012 through an application interface, such as a standalone application or a web browsing application, for example. The graphical user interface 1030, 1040, 1050, 1060, 1070 can be presented using hypertext markup language (HTML) and Java scripts, or a dedicated applet or application, or any other suitable interfacing means as would be known or understood in the art. The user 1012 can be presented with a variety of management, reporting, and/or scheduling tools or options. In the illustrated embodiment, the options are presented as selectable graphical elements or icons.

Figure 10A:
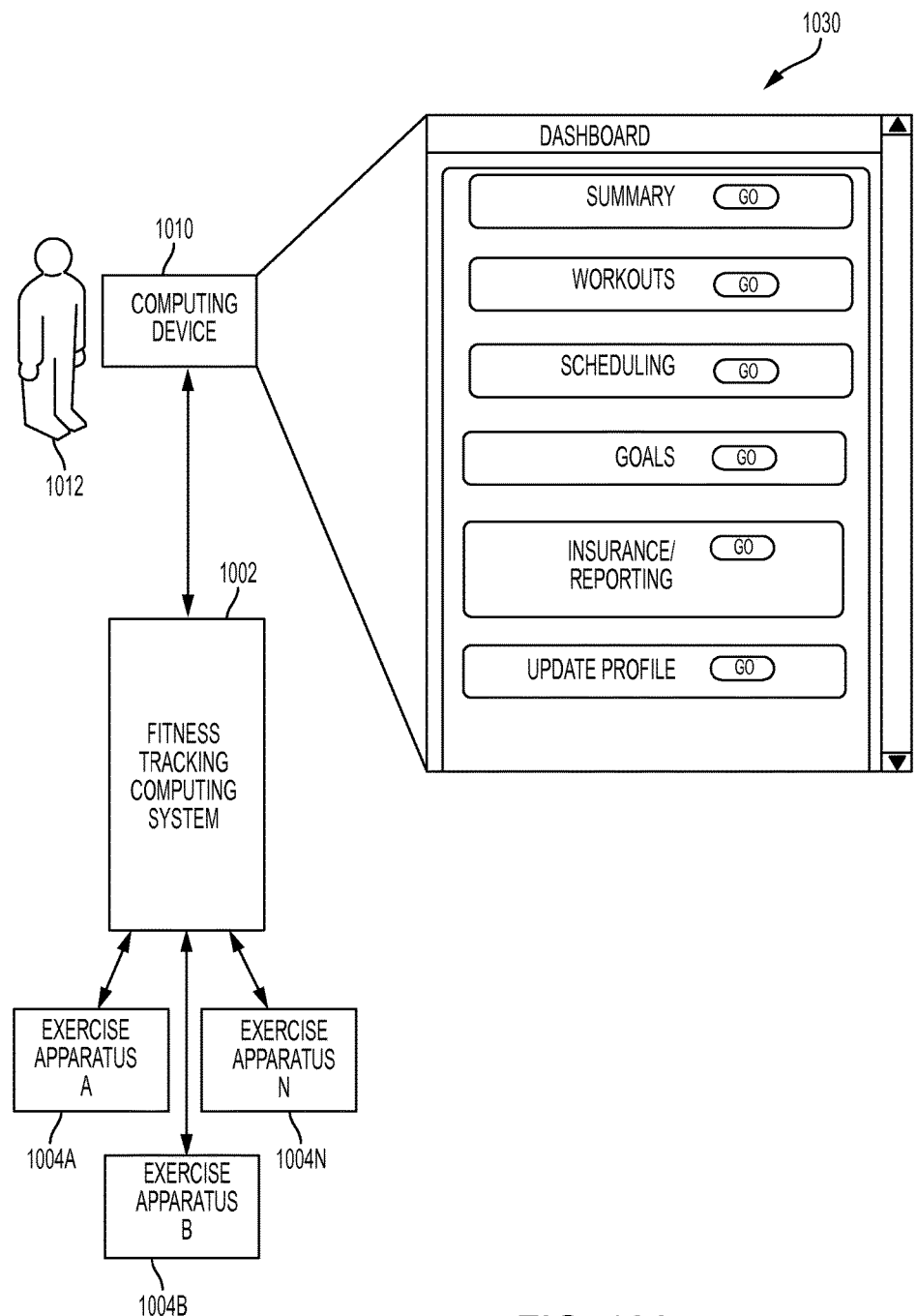
FIG. 10A-10E depict example simplified graphical user that can be presented on a display of a computing device.

Referring first to FIG. 10A, a simplified user dashboard is provided on the user interface 1030. As is to be appreciated, the particular content of the dashboard may vary based on the type of user 1012, with each user having a user account. In any event, in the illustrated example, the dashboard includes a summary portion, a workouts portion, a scheduling portion, a goals portions, an insurance/reporting portion, and an update profile portion. Through interactions with the various portions of the dashboard, the user 1012 can receive or input data to the fitness tracking computing system.

Figure 10B:
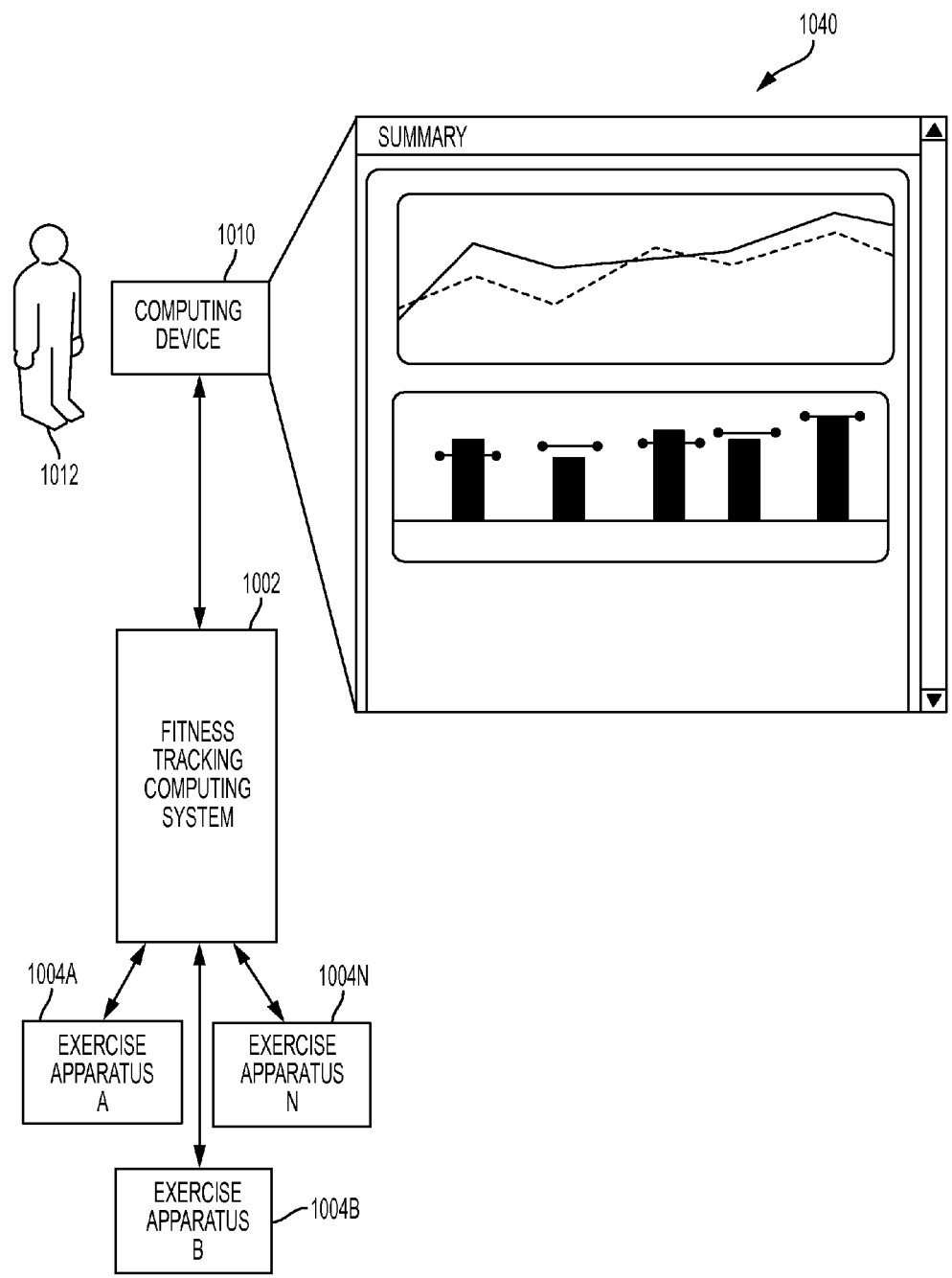

FIG. 10B depicts a simplified summary that can be provided on the user interface 1040. As is to be appreciated, the summary can provide a wide variety of useful content or data in any suitable presentation format. By way of example, a particular user's achieved results can be tracked against a set of goals.

Figure 10C:
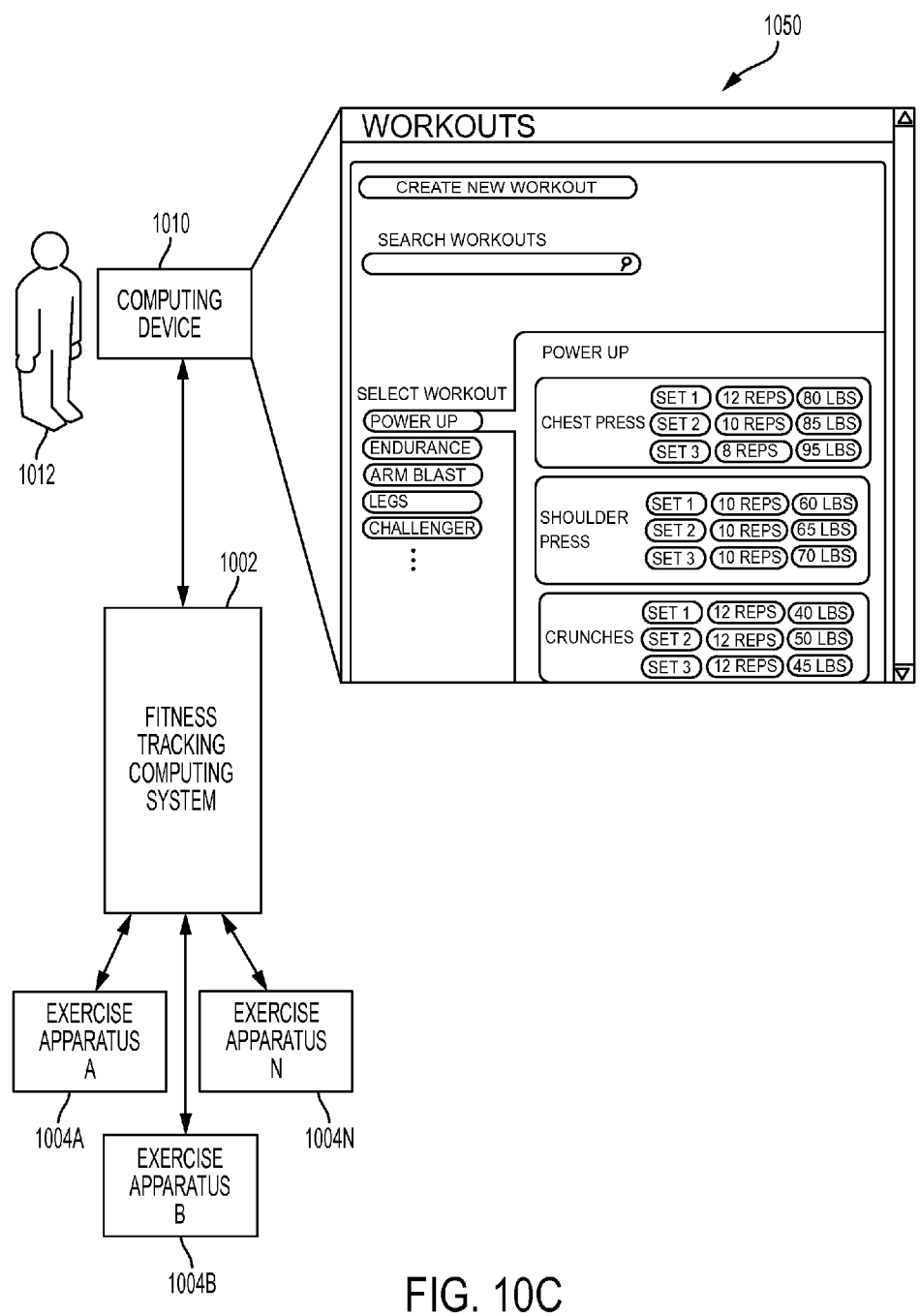

FIG. 10C depicts a simplified workout listing that can be provided on the user interface 1050. Through this interface a user can select a workout regimen, modify a workout regimen, build a workout regimen, and so forth. In some embodiments, one or more workout regimens may be sponsored by an affiliated entity.

Figure 10D:
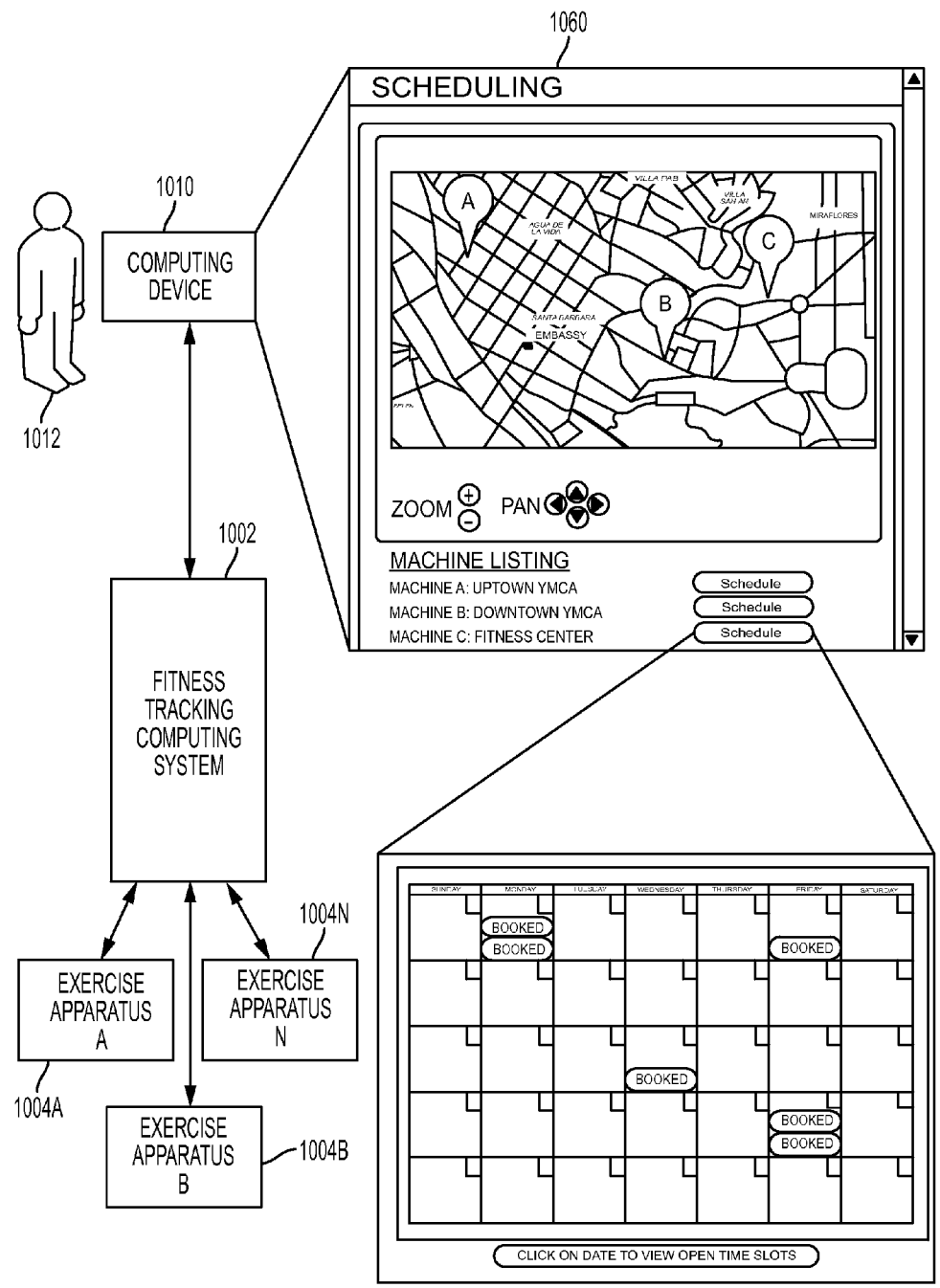

FIG. 10D depicts a simplified scheduling portal that can be provided on the user interface 1060. The scheduling portal can be used by, for example individual users, medical professionals, personal trainers, and so forth, to schedule the use of exercise apparatuses A-C. Along with the scheduled use, particular workout regimens can be assigned. In the illustrated embodiment, the user 1012 is provided with a map of the exercise apparatuses in a particular geographic area. The user 1012 can then select a particular apparatus and receive scheduling details. In the illustrated embodiment, a calendar is provided to the user 1012 through the interface and the user 1012 can then select a particular time/date to use the exercise apparatus.

Figure 10E:
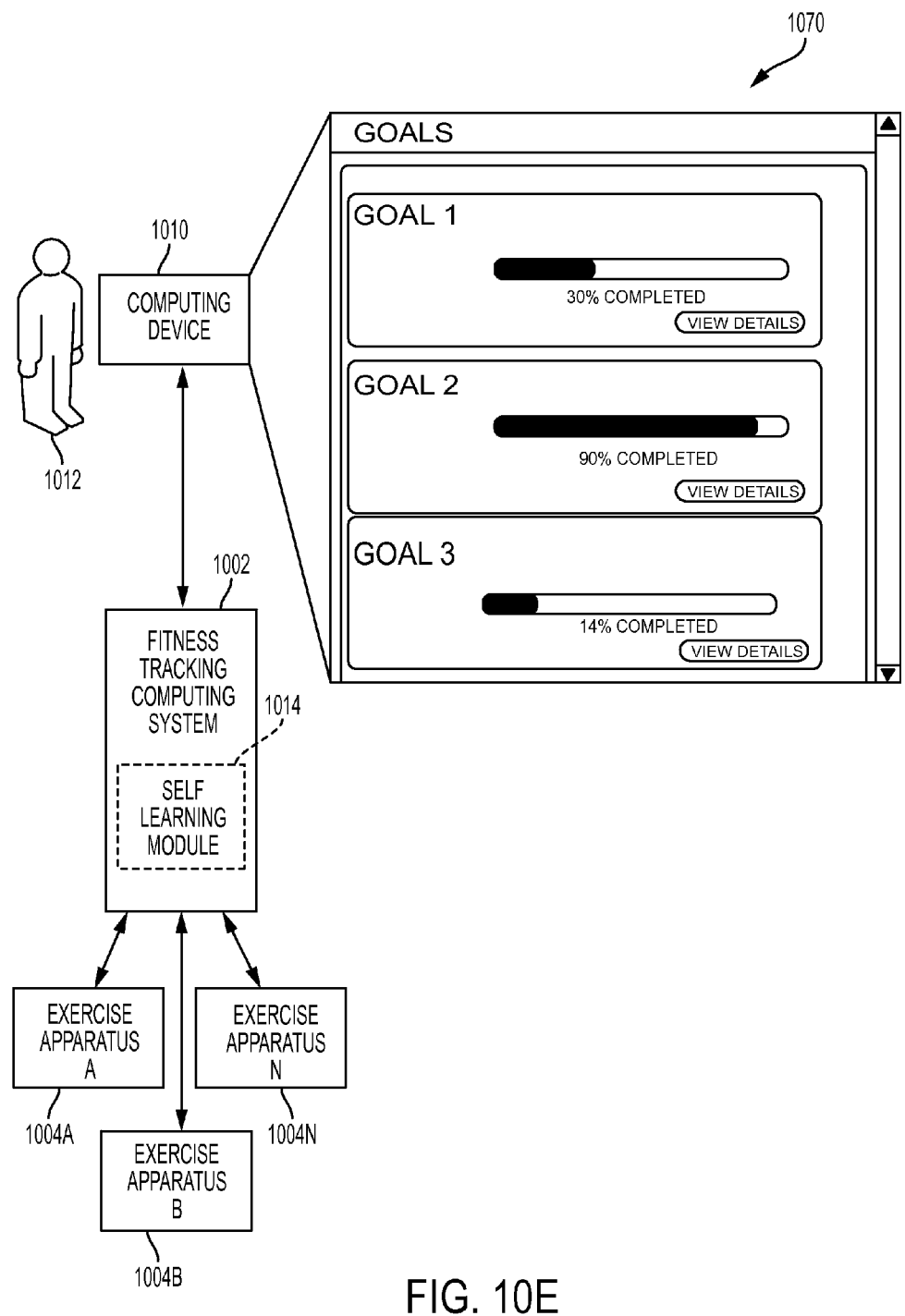

FIG. 10E depicts a simplified goal summary that can be provided on the user interface 1070. As is to be appreciated, the goals can be based on any number of quantifiable parameters that is based on the data received form the exercise apparatuses A-C.

In some embodiments, goals, exercises, workouts, and/or a variety other type of parameters can be suggested by the fitness tracking computing system 1002 to the user 1012. By way of example, the user 1012 may interact with one or more of the exercise apparatuses 1004-N over time in accordance with a pre-define fitness or rehabilitative regimen and the progression of the user's 1012 performance can be tracked. Based on the user's 1012 performance, or completion of certain milestones, the fitness tracking computing system 1002 can alter or recommend the regimen to better suit the user 1012 or otherwise adapt to the user's 1012 abilities or preferences. Thus, in accordance with certain embodiments, the fitness tracking computing system 1002 can comprise a self-learning module 1014 to monitor individual user's interaction with one or more exercise apparatuses and, in an automated fashion, make suggestions to the user 1012 based on the individual's past interactions or otherwise automatically modify a workout routine or an exercise parameter.

Self-learning modules in accordance with the present disclosure can be used in a variety of different implementations. For example, in some embodiments, a self-learning module can track a user's adherence to a particular pre-defined fitness regimen. Based on a user's under-performance or over-performance, the self-learning module can automatically augment the regimen. Under-performance may be identified, for example, by a user not completing certain workouts, not completing the instructed number of sets, or not completing the instructed number of repetitions. Furthermore, under-performance metrics can be asymmetric; such that it is determined a user is favoring a particular arm or leg during certain workouts. Over-performance may be identified, for example, by a user completing an instructed workout within a certain period of time, which may indicate the workout is not challenging. Over-performance may also be identified, for example, by the speed in which the user is moving various components of the exercise equipment, which may indicate the resistance lever is too low. In any event, based on the over-performance or under-performance, the self-learning module can modify the fitness regimen to alter various workouts, exercises and/or resistance amounts.

In yet another embodiment, the self-learning module can monitor a user's exercises, resistance levels, and/or other parameters over time (i.e., that are not necessarily tied to a particular regimen or predefined workout routine), and based on the user's success metrics, automatically recommend various workouts, exercises and/or resistance amounts. Success metrics include any number of factors, such as whether a user completed a particular number of sets, completed a particular number of repetitions, and/or utilized various exercises or configurations. By way of example, if a particular user is identified as focusing primarily on bicep-related exercises, the fitness tracking computing system 1002 can suggest tricep-related exercises. Similarly, if a user routinely completes a high number of repetitions and sets for a particular exercise, the fitness tracking computing system 1002 can suggest that the resistance level be increased. If a user, however, is not able to complete a certain number of repetitions and/or sets, the fitness tracking computing system 1002 can recommend a level of resistance that may be more appropriate for the user's abilities. In some embodiments, the user may input a muscle group (i.e., chest), and based on the user's previous success metrics, suggest an exercise to the user that will continue to challenge the user so the user can reach desired results. For example, resistance levels can be recommended by the fitness tracking computing system 1002 based on the particular user's success metrics related to the resistance levels of previously tracked exercise events. A self-learning module can provide the recommendations to users in any number of suitable formats or delivery techniques. For example, recommendations can be delivered to the user via the computing device 1010 (i.e., through a graphical user interface). Additionally or alternatively, the recommendations can be delivered to a graphical user interface on the exercise apparatus.

Figure 11:
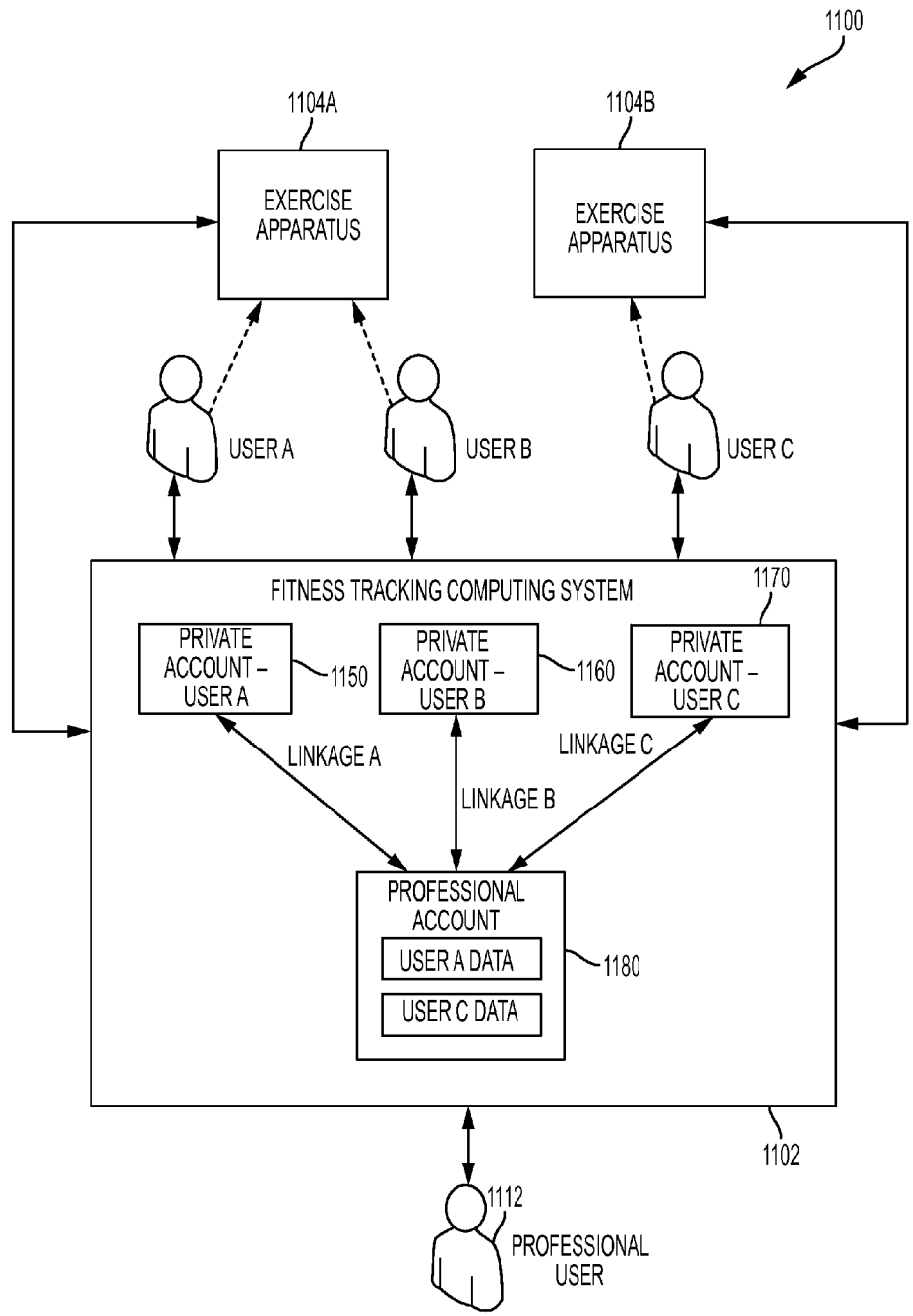
FIG. 11 depicts a fitness tracking computing system tracking a plurality of private accounts in accordance with one non-limiting embodiment.

The data presented in the graphical user interface 1030, 1040, 1050, 1060, 1070, along with other user data can be stored by fitness tracking computing systems in accordance with the present disclosure. In some embodiments, permissions, rules, roles, or other controls can be used to regulate which additional entities besides the user can access and/or modify the accounts of individual users. FIG. 11 depicts an example system diagram 1100 depicting a fitness tracking computing system 1102 maintaining a plurality of private accounts in accordance with one non-limiting embodiment. While example permission-based use cases are depicted in FIG. 11 for the purposes of illustration, it is to be appreciated that a wide variety of permission-based use cases can be facilitated by the systems and methods disclosed herein without departing from the present disclosure.

Referring first to User A, the fitness tracking computing system 1102 is depicted as maintaining a private account 1150 for User A. The private account 1150 can track, for example, various exercise activities of User A as gathered by exercise apparatus 1104A and/or any other exercise apparatus that is in networked communication with the fitness tracking computing system 1102 (e.g., exercise apparatus 1104B). A particular professional user 1112 can also interact with the fitness tracking computing system 1102 to access various data stored therein. While the role of the professional user 1112 can vary based on implementation, in some embodiments, the professional user 1112 can be a medical professional (such as a rehabilitative, physical therapist, etc.) a fitness professional (e.g., a personal trainer), a coach (e.g., team trainer, team medical staff, etc.), or other user (e.g., User C). This disclosure is not limited to any particular type of professional user 1112.

User A can optionally link the private account 1150 to a professional account 1180. Linkage A, as shown in FIG. 11, schematically depicts the sharing of information between the private account 1150 and the professional account 1180, as facilitated by the fitness tracking computing system 1102. The particular information shared between these two accounts can be controlled by rules and/or permissions as provided by User A, or other suitable entity or user. In some embodiments, linkage A is a read-only linkage, which allows the professional user 1112 to access some or all of the data in the private account 1150, but the professional user 1112 cannot write to the account (e.g., provide work-out regimens, etc.) In some embodiments, linkage A is a read/write linkage, which allows the professional user 1112 to access some or all of the data in the private account A and also write to the account. By allowing the professional user 1112 to post to the private account 1150, the professional user 1112 can submit work-out regimens, exercises, or other fitness related information or data to the User A by way of the private account 1150.

The private account 1150 is generally a repository for exercise-related data for User A. In the illustrated embodiment, User A has created its personal account 1150 prior to encountering a professional user 1112. At a particular point in time, such as upon receiving treatment by a physical therapist, working with a personal trainer, or otherwise engaging with a professional user 1112, User A may wish to share their previously collected exercise-related data with the professional user 1112. By granting read/write permissions to the professional user 1112 (as denoted by linkage A), the professional user 1112 can access previously gathered exercise-related data for User A. As the User A continues to interact with exercise apparatuses (such as exercise apparatus 1104A and/or 1104B), the professional user 1112 can monitor the results through their professional account 1180. Since the professional user 1112 has read/write privileges in this embodiment, the professional user 1112 can also push fitness related data to the private account 1150. In this regard, the professional user 1112 can push, for example, workouts, exercises, or other fitness regimens for User A to perform. User A's performance of these activities can then be tracked by the professional user 1112 through their professional account 1180. As is to be appreciated, the number of private accounts viewable through a professional account, as well as the scope of the data available, can vary based on the linkages established between the private accounts and the professional account. Furthermore, while not illustrated, a private account can be linked to a plurality of different professional accounts (i.e., one-to-many arrangement), with each linkage having similar or different permissions.

In some embodiments, User A can change or update the permissions of the professional user 1112 over time. For example, the professional user 1112 may be a personal trainer of User A that has full access to the private account A. At the termination of the relationship, User A can selectively retract all permissions that had been granted to the professional user 1112. In another embodiment, a physical therapist may have full access to private account A while User A completes a physical therapy process. Subsequent to the completion of the physical therapy process, User A may wish to demote the professional user 1112 (i.e., the physical therapist) from read/write access to read-only access. With read-only access, the physical therapist can still monitor (i.e., view) the exercise data gathered during User A's interaction with exercise apparatuses, even if these exercise apparatuses are located remote from the rehabilitative clinic.

Referring now to User B, another non-limiting use case will now be described merely for the purposes of illustration. In this embodiment, User B does not have an account with the fitness tracking computing system 1102 prior to engaging with the professional user 1112. In this embodiment, the professional user 1112 can be a physical therapist assisting User B in recovering from an injury or a fitness trainer working with a new client, for example. Private account 1160 can first be created for User B and then the professional user 1112 can be give read/write access to the private account 1160 in order to push certain workout routines or other exercises into the private account 1160. As described above, when User B interacts with the exercise apparatus 1104A, the particular fitness activities (as assigned by the professional user 1112) can be presented to User B for completion. User B's progression and completion of the various fitness activities can be logged by the fitness tracking computing system 1102 and be made available to the professional user 1112 by way of linkage B. Eventually, the relationship with the profession user can come to an end and Linkage B can also be severed. User B, however, can still retain their private account 1160 (as well as the data retained therein) so that as they continue to engage with various exercise apparatus, the private account 1160 can be accessed and updated.

Referring now to User C, the use case scenario is similar to that of User B in that when User C engages with the professional user 1112 and User C does not have a private account. A private account 1170 is created upon engagement with the professional user 1112. The private account 1170 can be populated over time with exercise-related data as User C interacts with one or more exercise apparatuses with the help of the professional user 1112. Eventually, User C can begin to interact with exercise apparatuses without the help of the professional user 1112. Nevertheless, the professional user 1112 can still have read-only rights (shown by linkage C) to allow the professional user 1112 to review the activity of User C.

Figure 12:
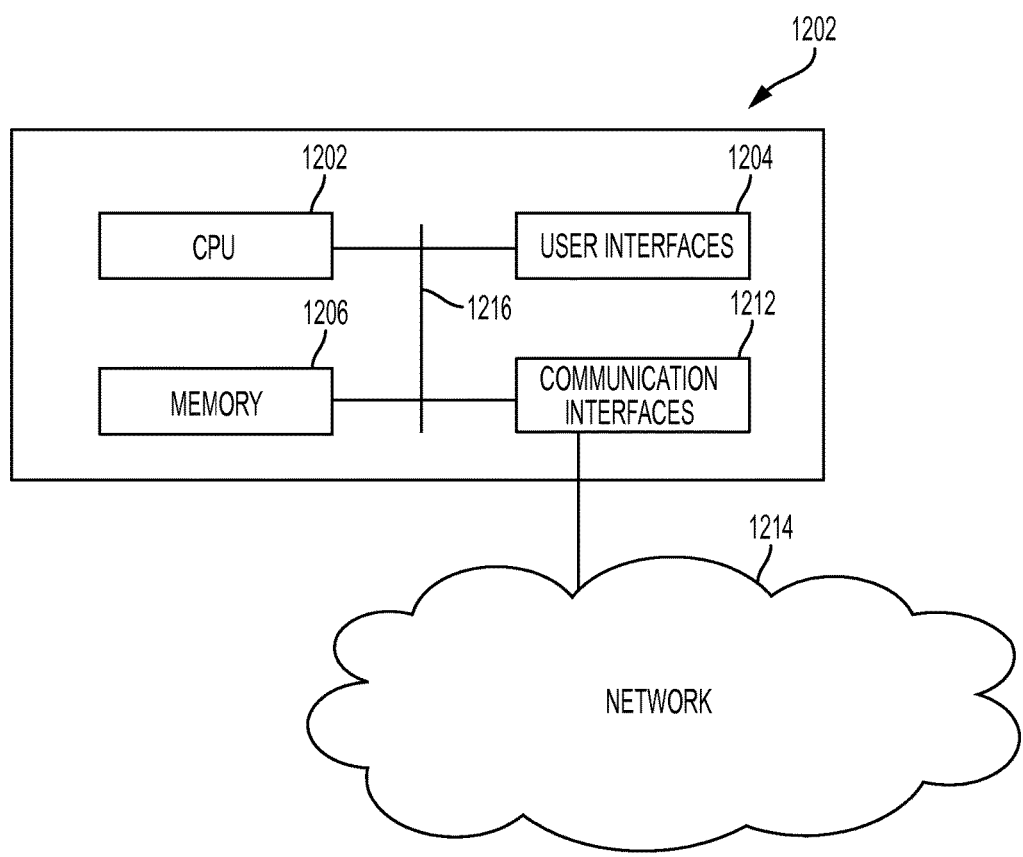
FIG. 12 depicts an example computing device.

The processes described herein can be performed on or between one or more computing devices. Referring now to FIG. 12, an example computing device 1200 is presented. A computing device 1200 can be a server, a computing device that is integrated with other systems or subsystems, a mobile computing device, a cloud-based computing capability, and so forth. The computing device 1200 can be any suitable computing device as would be understood in the art, including without limitation, a custom chip, an embedded processing device, a tablet computing device, a personal data assistant (PDA), a desktop, a laptop, a microcomputer, a minicomputer, a server, a mainframe, a fitness tracking computing system 102, 202, 302, 402, 602, 702, 802, 902, 1002, 1102 an exercise apparatus 104, 204, 304, 404, 504, 604A, 604B, 704A-N, 804A-N, 904, 1004A-N, 1104A-B or any other suitable programmable device. In various embodiments disclosed herein, a single component can be replaced by multiple components and multiple components can be replaced by a single component to perform a given function or functions. Except where such substitution would not be operative, such substitution is within the intended scope of the embodiments.

The computing device 1200 includes a processor 1202 that can be any suitable type of processing unit, for example a general purpose central processing unit (CPU), a reduced instruction set computer (RISC), a processor that has a pipeline or multiple processing capability including having multiple cores, a complex instruction set computer (CISC), a digital signal processor (DSP), an application specific integrated circuits (ASIC), a programmable logic devices (PLD), and a field programmable gate array (FPGA), among others. The computing resources can also include distributed computing devices, cloud computing resources, and virtual computing resources in general.

The computing device 1200 also includes one or more memories 1206, for example read only memory (ROM), random access memory (RAM), cache memory associated with the processor 1202, or other memories such as dynamic RAM (DRAM), static ram (SRAM), programmable ROM (PROM), electrically erasable PROM (EEPROM), flash memory, a removable memory card or disk, a solid state drive, and so forth. The computing device 1200 also includes storage media such as a storage device that can be configured to have multiple modules, such as magnetic disk drives, floppy drives, tape drives, hard drives, optical drives and media, magneto-optical drives and media, compact disk drives, Compact Disk Read Only Memory (CD-ROM), Compact Disk Recordable (CD-R), Compact Disk Rewriteable (CD-RW), a suitable type of Digital Versatile Disk (DVD) or BluRay disk, and so forth. Storage media such as flash drives, solid state hard drives, redundant array of individual disks (RAID), virtual drives, networked drives and other memory means including storage media on the processor 1202, or memories 1206 are also contemplated as storage devices. It can be appreciated that such memory can be internal or external with respect to operation of the disclosed embodiments. It can be appreciated that certain portions of the processes described herein can be performed using instructions stored on a computer-readable medium or media that direct a computer system to perform the process steps. Non-transitory computer-readable media, as used herein, comprises all computer-readable media except for transitory, propagating signals.

Network and communication interfaces 1212 can be configured to transmit to, or receive data from, other computing devices 1200 across a network 1214. The network and communication interfaces 1212 can be an Ethernet interface, a radio interface, a Universal Serial Bus (USB) interface, or any other suitable communications interface and can include receivers, transmitter, and transceivers. For purposes of clarity, a transceiver can be referred to as a receiver or a transmitter when referring to only the input or only the output functionality of the transceiver. Example communication interfaces 1212 can include wired data transmission links such as Ethernet and TCP/IP. The communication interfaces 1212 can include wireless protocols for interfacing with private or public networks 1214. For example, the network and communication interfaces 1212 and protocols can include interfaces for communicating with private wireless networks such as a WiFi network, one of the IEEE 802.11x family of networks, or another suitable wireless network. The network and communication interfaces 1212 can include interfaces and protocols for communicating with public wireless networks 1212, using for example wireless protocols used by cellular network providers, including Code Division Multiple Access (CDMA) and Global System for Mobile Communications (GSM). A computing device 1100 can use network and communication interfaces 1212 to communicate with hardware modules such as a database or data store, or one or more servers or other networked computing resources. Data can be encrypted or protected from unauthorized access.

In various configurations, the computing device 1200 can include a system bus 1216 for interconnecting the various components of the computing device 1200, or the computing device 1200 can be integrated into one or more chips such as programmable logic device or application specific integrated circuit (ASIC). The system bus 1216 can include a memory controller, a local bus, or a peripheral bus for supporting input and output devices 1204, and communication interfaces 1212. Example input and output devices 1204 include keyboards, keypads, gesture or graphical input devices, motion input devices, touchscreen interfaces, one or more displays, audio units, voice recognition units, vibratory devices, computer mice, and any other suitable user interface.

The processor 1202 and memory 1206 can include non-volatile memory for storing computer-readable instructions, data, data structures, program modules, code, microcode, and other software components for storing the computer-readable instructions in non-transitory computer-readable mediums in connection with the other hardware components for carrying out the methodologies described herein. Software components can include source code, compiled code, interpreted code, executable code, static code, dynamic code, encrypted code, or any other suitable type of code or computer instructions implemented using any suitable high-level, low-level, object-oriented, visual, compiled, or interpreted programming language.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these sorts of focused discussions would not facilitate a better understanding of the present invention, and therefore, a more detailed description of such elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein. Moreover, the processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A non-transitory computer-readable medium may also include memory storage that may be physical, virtual, permanent, temporary, semi-permanent and/or semi-temporary.

These and other embodiments of the systems and methods can be used as would be recognized by those skilled in the art. The above descriptions of various systems and methods are intended to illustrate specific examples and describe certain ways of making and using the systems disclosed and described here. These descriptions are neither intended to be nor should be taken as an exhaustive list of the possible ways in which these systems can be made and used. A number of modifications, including substitutions of systems between or among examples and variations among combinations can be made. Those modifications and variations should be apparent to those of ordinary skill in this area after having read this disclosure.

What is claimed is:

1. An exercise system, comprising:
    a plurality of exercise apparatuses, each of the plurality of exercise apparatuses comprising:
        a communication module for sending and receiving communications over a network;
        a resistance assembly;
        a housing containing the resistance assembly;
        an extension arm assembly operatively coupled to the resistance assembly, wherein the extension arm assembly is adjustable to a plurality of different positions, wherein each of the plurality of different positions corresponds to a different type of exercise performable on the exercise apparatus;
        at least one sensor configured to generate a signal based at least in part on movement of the extension arm assembly useable to determine whether the extension arm assembly is in a proper position;
    a fitness tracking computing system, the fitness tracking computing system configured to communicate with each of the plurality of exercise apparatuses over the network, the fitness tracking computing system configured to:
        transmit to one of the plurality of exercise apparatuses an exercise instruction, wherein the exercise instruction identifies at least one of the plurality of different positions for the extension arm assembly, the exercise instruction is associated with a type of exercise performable on the exercise apparatus;
        subsequent to the adjustment of the extension arm assembly based on the exercise instruction, receive from the one of the plurality of exercise apparatuses exercise event data; and
        store the exercise event data.

2. The exercise system of claim 1, wherein the communication module comprises a network interface.

3. The exercise system of claim 1, wherein the each of the plurality of exercise apparatuses comprises a user identification system configured to provide user identification indicia to the fitness tracking computing system.

4. The exercise system of claim 1, wherein the fitness tracking computing system comprises a scheduling module configured to track availability of each of the plurality of exercise apparatuses relative to a plurality of user schedules.

5. The exercise system of claim 1, wherein each of the plurality of exercise apparatuses are in communication with the fitness tracking computing system over a local area network (LAN).

6. The exercise system of claim 1, wherein each of the plurality of exercise apparatuses are in communication with the fitness tracking computing system over the Internet.

7. The exercise system of claim 1, wherein the fitness tracking computing system is configured to transmit an exercise report to a third party recipient.

8. The exercise system of claim 7, wherein the third party recipient is an insurance entity.

* * * * *